US009102945B2

(12) United States Patent
Ghulam Kadir et al.

(10) Patent No.: US 9,102,945 B2
(45) Date of Patent: Aug. 11, 2015

(54) CONSTITUTIVE PROMOTER FROM OIL PALM

(75) Inventors: Ahmad Parveez Ghulam Kadir, Selangor (MY); Siti Masura Subhi, Selangor (MY); Leslie Eng Ti Low, Selangor (MY)

(73) Assignee: MALAYSIAN PALM OIL BOARD, Kajang, Selangor (MY)

( * ) Notice: Subject to any disclaimer, the term of this patent is extended or adjusted under 35 U.S.C. 154(b) by 687 days.

(21) Appl. No.: 12/709,436

(22) Filed: Feb. 19, 2010

(65) Prior Publication Data

US 2010/0218274 A1 Aug. 26, 2010

(30) Foreign Application Priority Data

Feb. 20, 2009 (MY) ................................ PI 20090677

(51) Int. Cl.
*C12N 15/00* (2006.01)
*C12N 15/82* (2006.01)

(52) U.S. Cl.
CPC .......... *C12N 15/8216* (2013.01); *C12N 15/823* (2013.01); *C12N 15/8223* (2013.01)

(58) Field of Classification Search
USPC ....................... 435/6.1, 468, 410, 419, 320.1; 536/24.1; 800/278, 295
See application file for complete search history.

(56) References Cited

U.S. PATENT DOCUMENTS

| | | | |
|---|---|---|---|
| 4,873,192 A | 10/1989 | Kunkel | |
| 4,945,050 A | 7/1990 | Sanford et al. | |
| 5,231,020 A | 7/1993 | Jorgensen et al. | |
| 5,316,931 A | 5/1994 | Donson et al. | |
| 5,366,892 A | 11/1994 | Foncerrada et al. | |
| 5,380,831 A | 1/1995 | Adang et al. | |
| 5,436,391 A | 7/1995 | Fujimoto et al. | |
| 5,563,055 A | 10/1996 | Townsend et al. | |
| 5,589,367 A | 12/1996 | Donson et al. | |
| 5,593,881 A | 1/1997 | Thompson et al. | |
| 5,602,321 A | 2/1997 | John | |
| 5,605,793 A | 2/1997 | Stemmer | |
| 5,723,756 A | 3/1998 | Peferoen et al. | |
| 5,737,514 A | 4/1998 | Stiffler | |
| 5,747,450 A | 5/1998 | Ohba et al. | |
| 5,792,931 A | 8/1998 | Duvick et al. | |
| 5,837,458 A | 11/1998 | Minshull et al. | |
| 5,866,785 A | 2/1999 | Donson et al. | |
| 5,879,918 A | 3/1999 | Tomes et al. | |
| 5,886,244 A | 3/1999 | Tomes et al. | |
| 5,889,190 A | 3/1999 | Donson et al. | |
| 5,889,191 A | 3/1999 | Turpen | |
| 5,932,782 A | 8/1999 | Bidney | |
| 5,981,840 A | 11/1999 | Zhao et al. | |
| 6,072,050 A | 6/2000 | Bowen et al. | |
| 2006/0094088 A1* | 5/2006 | Picataggio et al. | ........... 435/134 |

OTHER PUBLICATIONS

Callis et al., J. Biol. Chem., 1990, vol. 265 (21), pp. 12486-12493.*
Annadana et al., Transgenic Research, Aug. 2002, vol. 11, No. 4, pp. 437-445.*
Altschul et al, "Basic local alignment search tool", J. Mol. Biol., (1990), 215(3):403-410.
Altschul, et al, "Gapped Blast and PSI-Blast: a new generation of protein database search programs", Nucleic Acids Res., (1997), 25(17):3389-3402.
Arencibia, et al, "Production of transgenic sugarcane (*Saccharum officinarum* l.,) plants by intact cell electroporation", Plant Cell Rep., (1995), 14(5):305-309.
Barcelo, et al, "Transgenic cereal (tritordeum) plants obtained at high efficiency by microprojectile bombardment of inflorescence tissue", The Plant Journal, (1994), 5(4):583-592.
Bevan, et al, "A chimaeric antibiotic resistance gene as a selectable marker for plant cell transformation", Nature, (1983), 304:184-187.
Bower, et al, "Transgenic sugarcane plants via microprojectile bombardment", The Plant Journal, (1992), 2(3):409-416.
Bretagne-Sagnard et al, "Selection of transgenic flax plants is facilitated by spectinomycin", Transgenic Res., (1996), 5:131-137.
Bytebier, et al, "T-DNA organization in tumor cultures and transgenic plants of the monocotyledon *Asparagus officinalis*", Proc. Natl. Acad. Sci., (1987), 84:5345-5349.
Chalfie et al, "Green fluorescent protein as a marker for gene expression", Science, (1994), 263(5148):802-805.
Chiu et al, "Engineered GFP as a vital reporter in plants", Current Biology, (1996), 6(3):325-330.
Chowdhury et al, "Evaluation of five promoters for use in transformation of oil palm (*Elaeis guineensis* Jacq.)," Plant Cell Rep., (1997), 16:277-281.
Christensen, et al, "Sequence analysis and transcriptional regulation by heat shock of polyubiquitin transcripts from maize", Plant Mol. Biol., (1989), 12(6):619-632.
Christensen, et al, "Ubiquitin promoter-based vectors for high-level expression of selectable and/or screenable marker genes in monocotyledonous plants", Transgenic Res., (1996), 5(3):213-218.
Christou, "Genetic transformation of crop plants using microprojectile bombardment", The Plant J., (1992), 2(3): 275-281.
Corpet et al, "Multiple sequence alignment with hierarchical clustering," Nucleic Acids Res., (1988), 16(22):10881-10890.
De Wet et al, "Firefly Luciferase Gene: Structure and Expression in Mammalian Cells", Mol. Cell. Biol., (1987), 7(2):725-737.
DeBlock et al, "Engineering herbicide resistance in plants by expression of a detoxifying enzyme", Embo J, (1987), 6(9):2513-2518.
D'Halluin, et al, "Transgenic Maize Plants by Tissue Electroporation", The Plant Cell, (1992), 4:1495-1505.
Doyle et al, "A rapid DNA isolation procedure for small quantities of fresh leaf tissue," Phytochemical Bulletin, (1987), 19(1):11-15.
Fraley et al, "Expression of bacterial genes in plant cells", Proc. Natl. Acad. Sci., (1983), 80:4803-4807.
Frame et al, "Production of fertile transgenic maize plants by silicon carbide whisker-mediated transformation", The Plant Journal, (1994), 6(6):941-948.

(Continued)

*Primary Examiner* — Phuong Bui

(74) *Attorney, Agent, or Firm* — Kilpatrick Townsend & Stockton LLP

(57) ABSTRACT

The present disclosure relates generally to gene promoters including promoters from oil palm plants, and to plants (including plants having genetic modifications) that include such promoters. The gene promoters of the present disclosure may be useful in facilitating expression of beneficial and/or desired phenotypic characteristics in plants and plant products.

24 Claims, 9 Drawing Sheets

(56) References Cited

OTHER PUBLICATIONS

Garfinkel et al, "Genetic analysis of crown gall: Fine structure map of the T-DNA by site-directed mutagenesis", Cell, (1981), 27(1):143-153.
Geiser et al, "The hypervariable region in the genes coding for entomopathogenic crystal proteins of *Bacillus thuringiensis*: nucleotide sequence of the kurhd1 gene of subsp. *kurstaki* HD1", Gene,(1986), 48(1):109-118.
Goff et al, "Transactivation of anthocyanin biosynthetic genes following transfer of B regulatory genes into maize tissues", EMBO J., (1990), 9(8):2517-2522.
Guerineau et al, "Sulfonamide resistance gene for plant transforamtion", Plant Mol. Biol., (1990), 15(1):127-136.
Henikoff et al., Amino acid substitution matrices from protein blocks, Proc. Natl. Acad. Sci., (1992), 89:10915-10919.
Herrera-Estrella et al, "Chimeric genes as dominant selectable markers in plant cells", EMBO J., (1983), 2(6):987-995.
Herrera-Estrella et al, "Expression of chimaeric genes transferred into plant cells using a Ti-plasmid-derived vector", Nature, (1983), 303:209-213.
Higgins et al, "Clustal: a package for performing multiple sequence alignment on a microcomputer," Gene, (1988), 73(1):237-244.
Higgins et al, "Fast and sensitive multiple sequence alignments on a microcomputer," Comput. Appl. Biosci., (1989), 5(2):151-153.
Hille et al, "Bleomycin resistance: a new dominant selectable marker for plant cell transformation", Plant Mol. Biol., (1986), 7:171-176.
Hoekema et al, "A binary plant vector strategy based on separation of vir-and T-region of the *Agrobacterium tumefaciens* Ti-plasmid", Nature, (1983), 303:179-180.
Hood et al, "The Hypervirulence of *Agrobacterium tumefaciens* A281 is Encoded in a Region of pTiBo542 Outside of T-DNA", J. Bacterol., (1986), 168(3):1291-1301.
Horn et al, Transgenic plants of Orchardgrass (*Dactylis glomerate* L.) from protoplasts, Plant Cell Rep., (1988), 7:469-472.
Horsch et al, "A Simple and General Method for Transferring Genes into Plants", Science, (1985), 227(4691):1229-1231.
Huang et al, "Parallelization of a local similarity algorithm," Cabios, (1992), 8(2):155-165.
Jahne et al, "Regeneration of transgenic, microspore-derived, fertile barley", Theor. Appl. Genet., (1994), 89(4):525-533.
Janssen et al, "Localized transient expression of GUS in leaf discs following cocultivation with *Agrobacterium*", Plant Mol. Biol., (1989), 14(1):61-72.
Jefferson, "Assaying Chimeric Genes in Plants: The GUS Gene Fusion System", Plant Mol. Biol. Rep., (1987), 5(1):387-405.
Jones et al, "A dominant nuclear streptomycin resistance marker for plant cell transformation", Mol. Gen. Genet, (1987), 210:86-91.
Jones et al, "Isolation of the tomato Cf-9 gene for resistance to *Cladosporium fulvum* by transposon tagging", Science, (1994), 266(5186):789-793.
Kaeppler et al, "Silicon carbide fiber-mediated DNA delivery into plant cells", Plant Cell Rep., (1990) 9(8):415-418.
Karlin et al, "Applications and statistics for multiple high-scoring segments in molecular sequences," Proc. Natl. Acad. Sci., (1993), 90:5873-5877.
Karlin et al, "Methods for assessing the statistical significance of molecular sequence features by using general scoring schemes," Proc. Natl. Acad. Sci.,(1990), 87:2264-2268.
Katz et al, "Cloning and Expression of the Tyrosinase Gene from *Streptomyces antibioticus* in *Streptomyces lividans*", J. Gen. Microbiol., (1983), 129:2703-2714.
Klein et al, "High-velocity microprojectiles for delivering nucleic acids into living cells," Nature, (1987), 327:70-73.
Klein et al, "Stable genetic transformation of intact Nicotiana cells by the particle bombardment process", Proc. Natl. Acad. Sci., (1988), 85:8502-8505.
Kloti et al, "Gene transfer by electroporation into intact scutellum cells of wheat embryos", Plant Cell Rep., (1993) 12:671-675.

Koncz et al, "The promoter of Ti-DNA gene 5 controls the tissue-specific expression of chimaeric genes carried by a novel type of *Agrobacterium* binary vector", Mol. Gen. Genet., (1986) 204(3):383-396.
Kuehnle et al, "Transformation of *Dendrobium* orchid using particle bombardment of protocorms", Plant Cell Rep., (1992) 11(9):484-488.
Kunkel, "Rapid and efficient site-specific mutagenesis without phenotypic selection," Proc. Natl. Acad. Sci., (1985), 82:488-492.
Kunkel, T., "Rapid and Efficient Site-Specific Mutagenesis Without Phenotypic Selection," Methods in Enzymology, (1987), 154:367-382.
Last et al, "pEmu: an improved promoter for gene expression in cereal cells", Theor. Appl. Genet., (1991), 81:581-588.
Laursen et al, "Production of fertile transgenic maize by electroporation of suspension culture cells", Plant Mol. Biol., (1994), 24(1):51-61.
Li et al., "Agronomic trait evaluation of field-grown transgenic rice plants containing the hygromycin resistance gene and the maize Activator element*1," Plant Science, (1995), 108(2):219-227.
Lorz et al., "Gene transfer to cereal cells mediated by protoplast transformation," Mol. Gen. Genet., (1985), 199:178-182.
Ludwig et al, "A regulatory gene as a novel visible marker for maize transformation", Science, (1990), 247:449-450.
Luehrsen et al, "Transient expression analysis in plants using firefly luciferase reporter gene", Methods Enzymol., (1992), 216:397-414.
Martin et al, "Map-based cloning of a protein kinase gene conferring disease resistance in tomato", Science, (1993), 262:1432-1436.
McCormick et al, "Leaf disc transformation of cultivated tomato (*L. esculentum*) using *Agrobacterium tumefaciens*", Plant Cell Reports, (1986), 5:81-84.
McElroy et al, "Isolation of an Efficient Actin Promoter for Use in Rice Transforamtion", Plant Cell., (1990), 2:163-171.
Mindrinos et al, "The *A. thaliana* disease resistance gene RPS2 encodes a protein containing a nucleotide-binding site and leucine-rich repeats," Cell, (1994), 78(6):1089-1099.
Moore et al, "Strategies for the in vitro evolution of protein function: enzyme evolution by random recombination of improved sequences", J. Mol. Biol., (1997), 272(3):336-347.
Mullis et al, "Specific synthesis of DNA in vitro via a polymerase-catalyzed chain reaction", Methods Enzymol., (1987), 155:335-350.
Murashige et al, "A Revised Medium for Rapid Growth and Bio Assay with Tobacco Tissue Cultures," Physiol. Plant., (1962), 15:473-497.
Murray et al, "Codon usage in plant genes", Nucleic Acids Res., (1989), 17:477-498.
Myers et al, "Optimal alignments in linear space", Cabios, (1988), 4(1):11-17.
Needleman et al, "A general method applicable to the search for similarities in the amino acid sequence of two proteins", J. Mol. Biol., (1970), 48(3):443-453.
Niedz et al., "Green fluorescent protein: an in vivo reporter of plant gene expression," Plant Cell Reports, (1995), 14(7):403-406.
Ow et al, "Transient and stable expression of the firefly luciferase gene in plant cells and transgenic plants", Science, (1986), 234:856-859.
Parveez, "Optimization of parameters involved in transformation of oil palm using the biolistic method", Ph.D. Thesis, (1998), Universiti Putra, Malaysia.
Paszkowski et al, "Direct gene transfer to plants", EMBO J., (1984), 3(12):2717-2722.
Pearson et al, "Improved tools for biological sequence comparison," Proc. Natl. Acad. Sci., (1988), 85:2444-2448.
Pearson et al, "Using the FASTA program to search protein and DNA sequence database," Methods Mol. Biol., (1994), 24:307-331.
Potrykus et al, "Molecular and general genetics of a hybrid foreign gene introduced into tobacco by direct gene transfer", Mol. Gen. Genet., (1985), 199:169-177.
Potrykus et al., Direct gene transfer of cells of a graminaceous monocot, Mol. Gen. Genet., (1985), 199(2):183-188.

(56) References Cited

OTHER PUBLICATIONS

Rajanaidu et al, "World-wide performance of DXP planting materials and future prospects." In Proceedings of 1995 PORIM National Oil Palm Conference.—Technologies in Plantation, The Way Forward. 11-12 Julai, Kuala Lumpur: Palm Oil Research Institute of Malaysia, (1995), 1-29.
Rashid et al., "Transgenic plant production mediated by *Agrobacterium* in Indica rice," Plant Cell Rep., (1996), 15(10):727-730.
Riggs et al, "Luciferase reporter gene cassettes for plant gene expression studies", Nucleic Acids Res., (1987), 15(19):8115.
Riggs et al, "Stable transformation of tobacco by electroporation: Evidence for plasmid concatenation", Proc. Natl. Acad. Sci., (1986), 83:5602-5606.
Salomon et al, "Genetic identification of functions of TR-DNA transcripts in octopine crown galls", EMBO J., (1984), 3(1):141-146.
Sambanthamurthi et al, "Genetic engineering in the oil palm," In Advances in Oil Palm Research, Malaysia Palm Oil Board, (2000), 1:284-331.
Schubert et al,"Cloning of the *Alcaligenes eutrophus* Genes for Synthesis of Poly-Beta-Hydroxybutyric Acid (PHB) and Synthesis of PHB in *Escherichia coli*", J. Bacteriol., (1988), 170:5837-5847.
Selden, et al, "Transfer RNA genes of Zea mays chloroplast DNA", Plant Mol. Biol., (1983), 2:141-153.
Shah et al, "Engineering herbicide tolerance in transgenic plants", Science, (1986), 233:478-481.
Shimamoto et al., "Fertile transgenic rice plants regenerated from transformed protoplasts," Nature, (1989), 338:274-276.
Smith et al., "Comparison of Biosequences," Advances in Applied Mathematics, (1981), 2(4):482-489.
Southern, "Detection of specific sequences among DNA fragments separated by gel electrophoresis", J. Mol. Biol., (1975), 98:503-517.
Stalker et al, "Herbicide resistance in transgenic plants expressing a bacterial detoxification gene", Science, (1988), 242:419-423.
Stemmer, "DNA shuffling by random fragmentation and reassembly: In vitro recombination for molecular evolution", Proc. Natl. Acad. Sci., (1994), 91:10747-10751.
Stemmer, "Rapid evolution of a protein in vitro by DNA shuffling", Nature, (1994), 370:389-391.
Sutcliffe, "Nucleotide sequence of the ampicillin resistance gene of *Escherichia coli* plasmid pBR322", Proc. Natl. Acad. Sci., (1978), 75(8):3737-3741.
Tarmizi et al, "Establishment of Oil Palm Embryogenic Suspension Cultures from Calli Derived from Various Sources," Proc. 11th National Biotechnology Seminar '99, Nov. 22-24, 1999, Melaka, Malaysia, 381-382.
Thillet et al, "Site-directed Mutagenesis of Mouse Dihydrofolate Reductase", J. Biol. Chem., (1988), 263 (25):12500-12508.
Topfer et al, "Uptake and Transient Expression of Chimeric Genes in Seed-Derived Embryos", The Plant Cell, (1989), 1:133-139.
Van Damme et al, "Molecular cloning of mannose-binding lectins from *Clivia miniata*", Plant Mol. Biol., (1994), 24(5):825-830.
Vancanneyt et al, Construction of an intron-containing marker gene: Splicing of the intron in transgenic plants and its use in monitoring early events in *Agrobacterium*-mediated plant transformation, Mol. Gen. Genet., 220(2):245-250 (1990).
Zambryski et al, "Ti plasmid vector for the introduction of DNA into plant cells without alteration of their normal regeneration capacity", EMBO J., (1983), 2(12):2143-2150.
Zeng et al, "RNA Isolation From Highly Viscous Samples Rich in Polyphenols and Polysaccharides," Plant. Mol. Biol. Reporter, (2002), 20:417a-417e.
Zhang et al, "Directed evolution of a fucosidase from a galactosidase by DNA shuffling and screening", Proc. Natl. Acad. Sci., (1997), 94:4504-4509.
Zukowsky et al, "Chromogenic identification of genetic regulatory signals in *Bacillus subtilis* based on expression of a cloned Pseudomonas gene", Proc. Natl. Acad. Sci., (1983), 80:1101-1105.

\* cited by examiner

```
  1 ATCCGCGGCT TCGATTTGAG AAAAATGAAG AGAAAGAGAG AGGGAGGAGG TCGATCTTCA
                       GT-1         POLLENLELAT52
 61 GTCTAAAGGG GAAGGGGTCT TCTTATAGAG AGTCCTAGGA CTCCGAAGGG TCCTGGGATT
       Dof-guard cell
121 CCTGATTCGC TTGGGTTTCG CTGGAGAGGA AGACTCCTAC CGGGAGTCTT CTTCCCGGTT
                                                              MYBCORE
181 GCTCTATTTT TTTTTTTTTT TTTGGCTGGG CTGGGCTTGG TTGGGCTGAT TTTGGGCTAT
         T-rich repeat 241 AACAGTTGAT ACTCAAATAA AGCTTCAATC AAGCTTGATT CAAGCACGCT TGTAGCTTAA
          GATA box  Dof-guard cell              ERE
301 TTCGAGCTCG AACATTATTG GTCATATGGT GCAAGATTTA AGGCTCCATT GTTAAATTAA
                                                              Dof-
361 AGCATACAAT ATGTAAGTAA GGTATATTAT ACTAATTTCA AGTCTAATTG AGTCGAGTTT
    guard cell             ROOTMOTIFAPOX1

AT-1
421 AGTCGGCCTC AATTCAAGCT TAATCTGAAA TTATTTTTAA CCCTCATGAA TCATGTTGGA
                                                UAS element
481 ACCTGAATCA AATATGTGCT CCAATGAAGA TGGATACGAT TTTATTTCCA ATCTGAGATC
                                        GATA box
541 GAGGTTACAT CAGGATTCGG TCTGGTGTAC CGCGAGCGAT GTCTCTTAAC ACACGGATTG
601 CCAACGTCCG CCCACCGATG AAAATCGAAC GGGCAGGATC AATCATCCTC CTTACGTACT
       ABA             GT-1
661 TCTCCACCGC AAGACACCAC AACTCAGTCT CAACCATATA AATTCCTCTT GCGGGCGCCA
                                             TATA BOX
721 TCCCAAAACC CTAGCACTCC CCGATCCCAT TTTCTCAAAC GCAAACCCTA AACCTAGCGG
                                                           M  Q  I  F
781 CGGCCGTCCT CCACCACCTG AGAGACGCCG TGCTCCATCG CCGGCAAGAT GCAGATCTTC
    GCCGGCAGGA GGTGGTGGAC TCTCTGCGGC ACGAGGTAGC GGCCGTTCTA CGTCTAGAAG
     V  K  T  L  T  G  K  T  I  T  L  E  V  E  S  S  D  T  I  D
841 GTGAAGACTC TGACGGGCAA GACCATCACC CTCGAGGTCG AGTCCTCGGA CACGATCGAC
    CACTTCTGAG ACTGCCCGTT CTGGTAGTGG GAGCTCCAGC TCAGGAGCCT GTGCTAGCTG
     N  V  K  A  K  I  Q  D  K  E  G  I  P  P  D  Q  Q  R  L  I
901 AACGTCAAGG CCAAGATCCA GGACAAAGAG GGCATCCCCC CGGACCAGCA GCGCCTCATC
    TTGCAGTTCC GGTTCTAGGT CCTGTTTCTC CCGTAGGGGG GCCTGGTCGT CGCGGAGTAG
     F  A  G  K  Q  L  E  D  G  R  T  L  A  D  Y  N  I  Q  K  E
961 TTCGCCGGAA AACAGCTCGA AGACGGCCGC ACCCTCGCCG ACTATAACAT CCAGAAGGAG
    AAGCGGCCTT TTGTCGAGCT TCTGCCGGCG TGGGAGCGGC TGATATTGTA GGTCTTCCTC
     S  T  L  H  L  V  L  R  L  R  G  G  A  K  K  R  K  K  T
1021 TCCACCCTCC ATCTAGTCCT CCGCCTCCGC GGTGGAGCCA AGAAGAGAAA GAAGAAGACG
     AGGTGGGAGG TAGATCAGGA GGCGGAGGCG CCACCTCGGT TCTTCTCTTT CTTCTTCTGC
      Y  T  K  P  K  K  I  K  H  K  K  K  V  K  L  A  V  L  Q
1081 TACACGAAGC CCAAGAAAAT CAAGCACAAG AAGAAGAAGG TCAAGCTTGC CGTGCTGCAA
     ATGTGCTTCG GGTTCTTTTA GTTCGTGTTC TTCTTCTTCC AGTTCGAACG GCACGACGTT
      F  Y  K  V  D  D  S  G  K  V  T  R  L  R  K  E  C  P  N  A
1141 TTTTACAAGG TGGACGACTC CGGAAAGGTG ACCAGACTCA GGAAGGAGTG CCCTAACGCC
     AAAATGTTCC ACCTGCTGAG GCCTTTCCAC TGGTCTGAGT CCTTCCTCAC GGGATTGCGG
      E  C  G  A  G  T  F  M  A  N  H  F  D  R  H  Y  C  G  K  C
1201 GAGTGTGGCG CCGGGACCTT CATGGCCAAC CACTTCGATC GCCACTACTG CGGCAAGTGC
     CTCACACCGC GGCCCTGGAA GTACCGGTTG GTGAAGCTAG CGGTGATGAC GCCGTTCACG
      G  L  T  Y  V  Y  Q  K  A  G  E  *
1261 GGCCTCACCT ACGTCTACCA GAAGGCCGGA GGTGAGTAAG GGATTGGACA GGAAGAGCCG
     CCGGAGTGGA TGCAGATGGT CTTCCGGCCT CCACTCATTC CCTAACCTGT CCTTCTCGGC
1321 ATTGGAGATC GATATATAGA GCTTTGCTTT AGTGGTTGCT TAGTTTCAAG TCTTAAGCCT
     TAACCTCTAG CTATATATCT CGAAACGAAA TCACCAACGA ATCAAAGTTC AGAATTCGGA
1381 GGAAGACAAA ATAATATTTG TGACCTAATT TTTGATTAAT GCTTTATGT GATGGATTAA
     CCTTCTGTTT TATTATAAAC ACTGGATTAA AAACTAATTA CGAAAATACA CTACCTAATT
1441 TTATGGTACA TTTGAAATTG GGATCTTATT ATTGCGAGAA TTGCTTGTTT GATTGTTAAA
     AATACCATGT AAACTTTAAC CCTAGAATAA TAACGCTCTT AACGAACAAA CTAACAATTT
1501 AAAAAAAA
     TTTTTTTT
```

FIGURE 5

Young leaflet from mature palm (YMLP)

Embriogenic calli (EC)
Embryoid
Green leaf
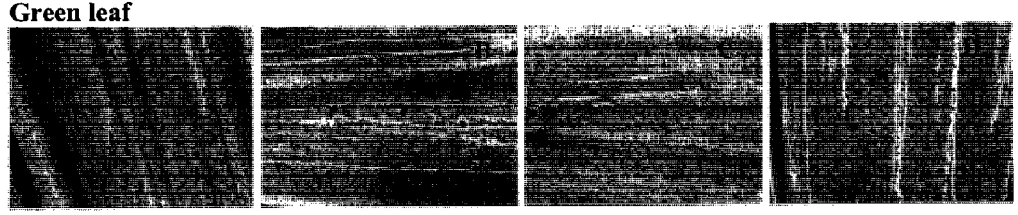
FIGURE 7
Stem /shoot tip

Mesocarp
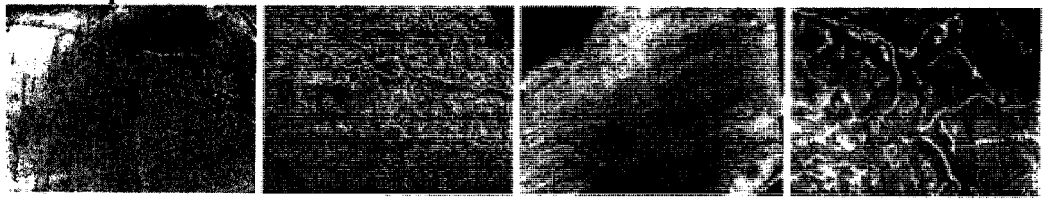
Immature embryo
Tobacco
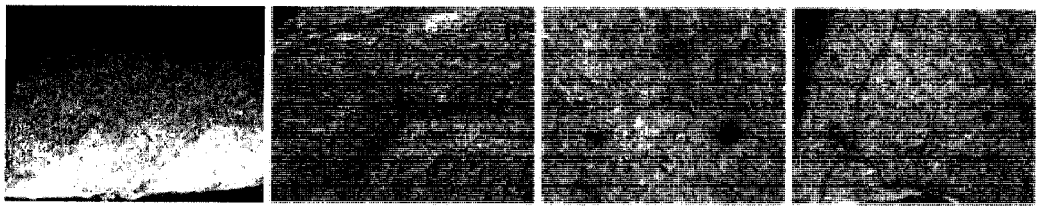
FIGURE 7 CONTINUED

US 9,102,945 B2

SEQUENCE LISTING

```
<160> NUMBER OF SEQ ID NOS: 5

<210> SEQ ID NO 1
<211> LENGTH: 1508
<212> TYPE: DNA
<213> ORGANISM: Elaeis guineensis
<220> FEATURE:
<221> NAME/KEY: CDS
<222> LOCATION: (829)..(1296)

<400> SEQUENCE: 1
atccgcggct tcgatttgag aaaaatgaag agaaagagag agggaggagg tcgatcttca      60
gtctaaaggg gaagggggtct tcttatagag agtcctagga ctccgaaggg tcctgggatt     120
cctgattcgc ttgggtttcg ctggagagga agactcctac cgggagtctt cttcccggtt     180
gctctatttt ttttttttttt tttggctggg ctggcttgg ttgggctgat tttgggctat     240
aacagttgat actcaaataa agcttcaatc aagcttgatt caagcacgct tgtagcttaa     300
ttcgagctcg aacattattg gtcatatggt gcaagattta aggctccatt gttaaattaa     360
agcatacaat atgtaagtaa ggtatattat actaatttca agtctaattg agtcgagttt     420
agtcggcctc aattcaagct taatctgaaa ttatttttaa ccctcatgaa tcatgttgga     480
acctgaatca aatatgtgct ccaatgaaga tggatacgat tttatttcca atctgagatc     540
gaggttacat caggattcgg tctggtgtac cgcgagcgat gtctcttaac acacggattg     600
ccaacgtccg cccaccgatg aaaatcgaac gggcaggatc aatcatcctc cttacgtact     660
tctccaccgc aagacaccac aactcagtct caaccatata aattcctctt gcgggcgcca     720
tcccaaaacc ctagcactcc ccgatcccat tttctcaaac gcaaacccta aacctagcgg     780
```

```
cggccgtcct ccaccacctg agagacgccg tgctccatcg ccggcaag atg cag atc      837
                                                     Met Gln Ile
                                                       1 ttc gtg aag act ctg acg ggc aag acc atc acc ctc gag gtc gag tcc      885
Phe Val Lys Thr Leu Thr Gly Lys Thr Ile Thr Leu Glu Val Glu Ser
      5              10                 15 tcg gac acg atc gac aac gtc aag gcc aag atc cag gac aaa gag ggc      933
Ser Asp Thr Ile Asp Asn Val Lys Ala Lys Ile Gln Asp Lys Glu Gly
 20              25                  30                  35 atc ccc ccg gac cag cag cgc ctc atc ttc gcc gga aaa cag ctc gaa      981
Ile Pro Pro Asp Gln Gln Arg Leu Ile Phe Ala Gly Lys Gln Leu Glu
                 40                  45                  50 gac ggc cgc acc ctc gcc gac tat aac atc cag aag gag tcc acc ctc     1029
Asp Gly Arg Thr Leu Ala Asp Tyr Asn Ile Gln Lys Glu Ser Thr Leu
             55                  60                  65 cat cta gtc ctc cgc ctc cgc ggt gga gcc aag aag aga aag aag aag     1077
His Leu Val Leu Arg Leu Arg Gly Gly Ala Lys Lys Arg Lys Lys Lys
         70                  75                  80 acg tac acg aag ccc aag aaa atc aag cac aag aag aag aag gtc aag     1125
Thr Tyr Thr Lys Pro Lys Lys Ile Lys His Lys Lys Lys Lys Val Lys
     85                  90                  95 ctt gcc gtg ctg caa ttt tac aag gtg gac gac tcc gga aag gtg acc     1173
Leu Ala Val Leu Gln Phe Tyr Lys Val Asp Asp Ser Gly Lys Val Thr
100                 105                 110                 115 aga ctc agg aag gag tgc cct aac gcc gag tgt ggc gcc ggg acc ttc     1221
Arg Leu Arg Lys Glu Cys Pro Asn Ala Glu Cys Gly Ala Gly Thr Phe
                120                 125                 130 atg gcc aac cac ttc gat cgc cac tac tgc ggc aag tgc ggc ctc acc     1269
Met Ala Asn His Phe Asp Arg His Tyr Cys Gly Lys Cys Gly Leu Thr
            135                 140                 145 tac gtc tac cag aag gcc gga ggt gag taagggattg gacaggaaga           1316
Tyr Val Tyr Gln Lys Ala Gly Gly Glu
        150                 155 gccgattgga gatcgatata tagagctttg ctttagtggt tgcttagttt caagtcttaa   1376
gcctggaaga caaaataata tttgtgacct aattttttgat taatgctttt atgtgatgga  1436
ttaattatgg tacatttgaa attgggatct tattattgcg agaattgctt gtttgattgt   1496
taaaaaaaaa aa                                                       1508

<210> SEQ ID NO 2
<211> LENGTH: 828
<212> TYPE: DNA
<213> ORGANISM: Elaeis guineensis

<400> SEQUENCE: 2
atccgcggct tcgatttgag aaaaatgaag agaaagagag agggaggagg tcgatcttca     60
gtctaaaggg gaagggtct tcttatagag agtcctagga ctccgaaggg tcctgggatt    120
cctgattcgc ttgggtttcg ctggagagga agactcctac cgggagtctt cttcccggtt   180
gctctatttt tttttttttt tttggctggg ctgggcttgg ttgggctgat tttgggctat   240
aacagttgat actcaaataa agcttcaatc aagcttgatt caagcacgct tgtagcttaa   300
ttcgagctcg aacattattg gtcatatggt gcaagattta aggctccatt gttaaattaa   360
agcatacaat atgtaagtaa ggtatattat actaatttca agtctaattg agtcgagttt   420
agtcggcctc aattcaagct taatctgaaa ttattttttaa ccctcatgaa tcatgttgga   480
acctgaatca aatatgtgct ccaatgaaga tggatacgat tttatttcca atctgagatc    540
```

```
gaggttacat caggattcgg tctggtgtac cgcgagcgat gtctcttaac acacggattg    600
ccaacgtccg cccaccgatg aaaatcgaac gggcaggatc aatcatcctc cttacgtact    660
tctccaccgc aagacaccac aactcagtct caaccatata aattcctctt gcgggcgcca    720
tcccaaaacc ctagcactcc ccgatcccat tttctcaaac gcaaaccctaa aacctagcgg    780 cggccgtcct ccaccacctg agagacgccg tgctccatcg ccggcaag                 828

<210> SEQ ID NO 3
<211> LENGTH: 471
<212> TYPE: DNA
<213> ORGANISM: Elaeis guineensis

<400> SEQUENCE: 3
atgcagatct tcgtgaagac tctgacgggc aagaccatca ccctcgaggt cgagtcctcg    60
gacacgatcg acaacgtcaa ggccaagatc caggacaaag agggcatccc cccggaccag   120
cagcgcctca tcttcgccgg aaaacagctc gaagacggcc gcaccctcgc cgactataac   180
atccagaagg agtccaccct ccatctagtc ctccgcctcc gcgtgggagc caagaagaga   240
aagaagaaga cgtacacgaa gcccaagaaa atcaagcaca agaagaagaa ggtcaagctt   300
gccgtgctgc aattttacaa ggtggacgac tccggaaagg tgaccagact caggaaggag   360
tgccctaacg ccgagtgtgg cgccgggacc ttcatggcca accacttcga tcgccactac   420
tgcggcaagt gcggcctcac ctacgtctac cagaaggccg gaggtgagta a             471

<210> SEQ ID NO 4
<211> LENGTH: 156
<212> TYPE: PRT
<213> ORGANISM: Elaeis guineensis

<400> SEQUENCE: 4

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ala Asp Tyr Asn Ile Gln Lys Glu
    50                  55                  60

Ser Thr Leu His Leu Val Leu Arg Leu Arg Gly Ala Lys Lys Arg
65                  70                  75                  80

Lys Lys Lys Thr Tyr Thr Lys Pro Lys Lys Ile Lys His Lys Lys Lys
                85                  90                  95

Lys Val Lys Leu Ala Val Leu Gln Phe Tyr Lys Val Asp Asp Ser Gly
            100                 105                 110

Lys Val Thr Arg Leu Arg Lys Glu Cys Pro Asn Ala Glu Cys Gly Ala
        115                 120                 125

Gly Thr Phe Met Ala Asn His Phe Asp Arg His Tyr Cys Gly Lys Cys
    130                 135                 140

Gly Leu Thr Tyr Val Tyr Gln Lys Ala Gly Gly Glu
145                 150                 155

<210> SEQ ID NO 5
<211> LENGTH: 209
<212> TYPE: DNA
<213> ORGANISM: Elaeis guineensis
```

```
<400> SEQUENCE: 5
gggattggac aggaagagcc gattggagat cgatatatag agctttgctt tagtggttgc      60
ttagtttcaa gtcttaagcc tggaagacaa aataatattt gtgacctaat ttttgattaa     120
tgcttttatg tgatggatta attatggtac atttgaaatt gggatcttat tattgcgaga    180
attgcttgtt tgattgttaa aaaaaaaaa                                       209
```

CONSTITUTIVE PROMOTER FROM OIL PALM

CROSS REFERENCE TO RELATED APPLICATIONS

This application claims priority to Malaysian Application No. PI20090677 filed Feb. 20, 2009 incorporated herein by reference in its entirety.

SEQUENCE LISTING

The instant application contains a Sequence Listing which has been submitted via EFS-Web and is hereby incorporated by reference in its entirety. Said ASCII copy, created on May 5, 2010, is named 06935907.txt and is 7,932 bytes in size.

FIELD OF THE INVENTION

The present invention relates to gene promoters and/or to plants (for example oil palm plants) having genetic modifications.

BACKGROUND

Reference to any prior art in this specification is not, and should not be taken as, an acknowledgement or any form of suggestion that this prior art forms part of the common general knowledge in Malaysia, Australia or any other country.

The demand for oils and fats is expected to increase dramatically with the increase in world population and the need for sustainable resources. Oil palm (*Elaeis guineensis* and *Elaeis oleifera*), which produces the palm oil and palm kernel oil, is the highest yielding oil crop in the world and was forecasted to contribute around a quarter of the world's oil and fats demand by the year 2020 (Rajanaidu, and Jalani, World-wide performance of DXP planting materials and future prospects. *In Proceedings of* 1995 *PORIM National Oil Palm Conference.—Technologies in Plantation*, The Way Forward. 11-12 Julai, Kuala Lumpur: Palm Oil Research Institute of Malaysia, pp. 1-29, 1995). Due to the demand, there is a need to increase the quality and yield of palm oil and palm kernel oil and to rapidly develop new characteristics when required.

Oil palm is the most important commercial crop in Malaysia. It has been identified as the most likely candidate for the development of a large scale production and renewal plant (Ravigadevi et al, *Genetic engineering in oil palm. In Advances in Oil Palm Research.* (eds). Yusof, Jalani, and Chan *Malaysia Palm Oil Board.* 1:284-331, 2000) for palm oil-derived chemicals. The ultimate aim is to genetically engineer the oil palm so as to modify its oil composition in order to expand its applicability. Moreover, the advancement in the genetic transformation of plants has made it possible to transfer foreign genes into the genome of oil palm (Parveez, *Optimization of parameters involved in transformation of oil palm using the biolistic method*. PhD. Thesis. Universiti Putra Malaysia, 1998). Introduction of foreign genes via genetic engineering will enhance the productivity and value of oil palm.

Genetic engineering is a specialized method of improving plant quality by introducing foreign genes into the whole plant by genetic transformation. Genetic engineering processes are often unique to particular plants. An efficient tissue culture system is required in order to produce genetically modified plants after successful delivery and integration of genetic material into cells which regenerate into a whole plant. The introduced genetic material needs to be present in all cells of the regenerated plant and its progeny. The expression of the genetic material may be in all cells or in particular cells, tissues or organelles. Tissue-specific and constitutive promoters are, therefore, required.

SUMMARY

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Nucleotide and amino acid sequences are referred to by a sequence identifier number (SEQ ID NO:1 and SEQ ID NO:2, etc which correspond to the equivalent designations <400> 1, <400> 2, respectively). A summary of the sequence identifiers is provided in Table 1. A sequence listing is provided after the claims.

The present disclosure provides a promoter for use in the genetic manipulation of plants and more particularly oil palm plants of the species *Elaeis*. In certain embodiments a promoter as described herein is isolatable from *Elaeis* sp. and may be referred to as the "UEP1 promoter". Reference to the "UEP1 promoter" includes the UEP1 promoter itself as well as functional homologs, derivatives and equivalents thereof. In accordance with the present disclosure, oil palm plants comprising the UEP1 promoter operably linked to genetic material constitutively express the genetic material to produce mRNA or other RNA species or peptides, polypeptides or proteins. The genetic material may, for example, confer resistance to a herbicide, resistance to a plant pest including a virus, insect, fungus or microbe, confer a defense to a disease condition, or the genetic material may modify lipids and non-lipid components of palm oil resulting in improved quality of palm oil or altered or improved production of industrial oils and chemicals. The genetic material may also encode nutraceutical or pharmaceutical molecules. The UEP1 promoter may be used in a range of plants in addition to *Elaeis* sp.

Accordingly, one aspect of the present disclosure provides an isolated nucleic acid molecule comprising a UEP1 promoter.

Another aspect of the present disclosure provides a method for the generation of a DNA construct comprising a UEP1 promoter operably linked or linkable to a heterologous nucleic sequence of interest. The method comprising introducing into a plasmid a UEP1 promoter and either a heterologous nucleic acid sequence operably linked thereto or restriction endonuclease means to insert a heterologous sequence.

A particular aspect of the present disclosure contemplates a method for expressing a nucleotide sequence in a plant or a parent of such a plant, the method comprising introducing into a plant a DNA construct, the DNA construct comprising a UEP1 promoter operably linked to a heterologous nucleotide sequence of interest.

Yet another aspect of the present disclosure provides a method for expressing a nucleotide sequence in a plant cell, the method comprising introducing into a plant cell or parent of such a plant cell a DNA construct comprising a UEP1 promoter operably linked to a heterologous nucleotide sequence of interest.

Still another aspect of the present disclosure contemplates a method of genetically modifying a plant whereby a heterologous nucleotide sequence encoding a proteinaceous product or double-stranded RNA or other RNA species which confers resistance to a herbicide, resistance to a pest including a pathogenic agent or confers a defense to a disease condition, or which confers a modification lipids and non-lipid components of palm oil is expressed, the method comprising introducing the heterologous nucleotide sequence operably linked to a UEP1 promoter into a cell of a plant, regenerating a plant from the cell wherein the regenerated plant and its progeny are genetically modified.

Yet another aspect the present disclosure is directed to for the use of a UEP1 promoter in the generation of a genetically modified plant or its progeny or products therefrom.

Reference to a "UEP1 promoter" includes the UEP1 promoter itself as well as a functional homolog, derivative or equivalent thereof, comprising a nucleotide sequence expressible in *Elaeis* species selected from:
 a. a nucleotide sequence comprised within the 5' portion of SEQ ID NO:1 or a complement thereof;
 b. a nucleotide sequence set forth in SEQ ID NO:2 or complement thereof;
 c. a nucleotide sequence of a) or b) comprised within a plasmid, or a full-length complement thereof;
 d. a nucleotide sequence comprising a fragment of a), b) or c), wherein the sequence initiates transcription in a plant cell;
 e. a nucleotide sequence comprising a sequence having at least 85% sequence identity to the sequence set forth in SEQ ID NO:1 or 2, wherein the sequence initiates transcription in the plant cell; and
 f. a nucleotide sequence which hybridizes to SEQ ID NO 1 or 2, or complement thereof under low stringency conditions and which initiates transcription in a plant cell.

The present disclosure includes an isolated nucleic acid molecule, comprising a promoter from the gene encoding UEP1, the promoter comprising a nucleotide sequence selected from the group consisting of:
 a. a nucleotide sequence comprised within the 5' portion of SEQ ID NO:1 or a complement thereof;
 b. a nucleotide sequence set forth in SEQ ID NO:2 or complement thereof;
 c. a nucleotide sequence of a) or b) comprised within a plasmid, or a full-length complement thereof;
 d. a nucleotide sequence comprising a fragment of a), b) or c), wherein said sequence initiates transcription in a plant cell;
 e. a nucleotide sequence comprising a sequence having at least 85% sequence identity to the sequence set forth in SEQ ID NO:1 or 2, wherein the sequence initiates transcription in the plant cell; and
 f. a nucleotide sequence which hybridizes to SEQ ID NO 1 or 2 or complement thereof under low stringency conditions and which initiates transcription in a plant cell.

In a particular embodiment, the present disclosure provides an isolated nucleic acid molecule comprising the nucleotide sequence set forth in SEQ ID NO:2 or sequence having at least 85% identity thereto or which hybridizes to SEQ ID NO:2 or a complement thereof under low stringency conditions and which functions as a promoter of a cell of an *Elaeis* species.

The term "UEP1" refers to the gene encoding ubiquitin extension protein 1. The promoter associated with this gene is the "UEP1 promoter".

Whilst the UEP1 promoter of the present disclosure may be particularly useful in the genetic manipulation of *Elaeis* species, the present disclosure extends to its use in a range of plants including crop plants, ornamental flowering plants and other plant types. Hence, another aspect of the present disclosure is directed to a genetically modified plant comprising a UEP1 promoter operably linked to a heterologous nucleotide sequence which upon expression conferred a desired trait on the plant or its progeny or in a product of the plant.

In a particular embodiment, the plant is an oil palm plant and the product is oil palm.

A summary of the sequence identifiers referred to herein is in Table 1.

TABLE 1

Summary of sequence identifiers

| SEQ ID NO | DESCRIPTION |
|---|---|
| 1 | Nucleotide sequence of ubiquitin extension protein (UEP) gene |
| 2 | Nucleotide sequence of the 5' region of UEP gene |
| 3 | Nucleotide sequence of coding region of UEP gene |
| 4 | Amino acid sequence of UEP gene |
| 5 | 3' Nucleotide sequence of UEP gene |

BRIEF DESCRIPTION OF THE FIGURES

Some figures contain color representations or entities. Color photographs are available from the Patentee upon request or from an appropriate Patent Office. A fee may be imposed if obtained from a Patent Office.

FIG. 5 is a DNA sequence (SEQ ID NO: 1) and map of the oil palm UEP1 genomic clone. The sequence is numbered from the 5' PvuII site. The UEP1 coding region begins at residue 829 and extends to residue 1296. The predicted protein sequence (SEQ ID NO: 4) is shown extending to the first stop codon 5' to the initiating methionine (M). Position of putative transcription start site is indicated with large and bold font. The putative TATA box, CAAT box and other putative cis-elements are underlined and labeled.

FIG. 7 are photographic representations of the comparison of transient histochemical assay on various oil palm tissues and tobacco bombarded with plasmid carrying gus gene driven by different promoters. For immature embryo, the tissue was not bombarded with pBI221 because of limited sample. A) none (bombarded without plasmid DNA), B) pAHC25 (Ubi1), C) pBI221 (CaMV35S) and D) pUEP1 (uep1).

DETAILED DESCRIPTION

Figure 1:
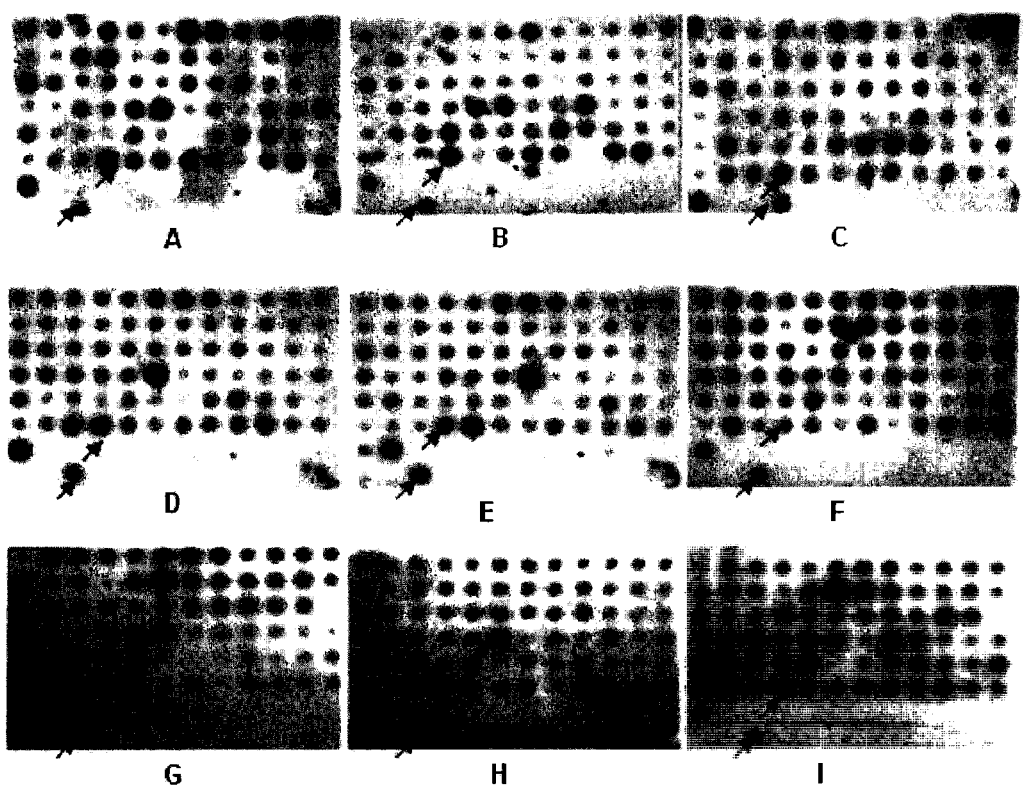
FIG. 1 are photographic representations showing a reverse northern analysis to screen the expression pattern of 73 cDNA clones generated through a microarray approach. The membranes were hybridized with first strand cDNA pooled from A) mesocarp 5 weeks after anthesis (WAA), B) mesocarp 9 WAA, C) mesocarp 14 WAA, D) mesocarp 15 WAA, E) mesocarp 17 WAA, F) kernel 14 WAA, G) kernel 17 WAA, H) frond, I) flower. Blue and red arrows indicate the location of the pOPSFB-1301 cDNA clone and ribosomal DNA, respectively.

The present disclosure is directed to an isolated nucleic acid molecule which defines a constitutive promoter, the ubiquitin extension protein 1 (UEP1) gene promoter (UEP1 promoter), from a species of *Elaeis* and to the generation of plasmid constructs and genetically modified plants comprising the UEP1 promoter.

The ability to produce genetically modified plants such as oil palm plants with the UEP1 promoter operably linked to particular genetic material facilitates the further improvement or modification of plants. For example, in relation to oil plants introduction of useful traits include, for example, plants which exhibit increased yield of oil, are resistant to certain diseases including those caused by pathogenic agents, have modified lipids and non-lipid components of palm oil and improved quality of palm oil or improved production of industrial oils and chemicals. The traits may also include the production of nutraceutical and pharmaceutical compounds.

Embodiments of the present disclosure are predicated in part on the identification of the constitutive promoter, UEP1, from *Elaeis* species which facilitates expression of genetic material which is operably linked to the promoter. The UEP1 promoter is defined as:
  a. a nucleotide sequence comprised within the 5' portion of SEQ ID NO:1 or a complement thereof;
  b. a nucleotide sequence set forth in SEQ ID NO:2 or complement thereof;
  c. a nucleotide sequence of a) or b) comprised within a plasmid, or a full-length complement thereof;
  d. a nucleotide sequence comprising a fragment of a), b) or c), wherein the sequence initiates transcription in a plant cell;
  e. a nucleotide sequence comprising a sequence having at least 85% sequence identity to the sequence set forth in SEQ ID NO:1 or 2, wherein the sequence initiates transcription in the plant cell; and
  f. a nucleotide sequence which hybridizes to SEQ ID NO:1 or 2 or complement thereof under low stringency conditions and which initiates transcription in a plant cell.

In a particular embodiment, the present disclosure provides an isolated nucleic acid molecule comprising the nucleotide sequence set forth in SEQ ID NO:2 or sequence having at least 85% identity thereto or which hybridizes to SEQ ID NO:2 or a complement thereof under low stringency conditions and which functions as a promoter of a cell of an *Elaeis* species.

The promoter sequences of the present disclosure may be useful for expressing operably linked or linkable nucleotide sequences in a constitutive manner in a range of plants including species of *Elaeis*. The sequences may also find use in the construction of expression vectors for subsequent transformation into plants of interest, as probes for the isolation of other gene promoters, as molecular markers, and the like. The UEP1 promoter of the present invention was isolated from the oil palm plant, *Elaeis* sp. An example of a specific method that may be used to obtain a UEP1 promoter of the present disclosure is described in the Examples in this specification.

Hence, one aspect of the present disclosure is directed to the isolation of a nucleic acid molecule comprising a constitutive UEP1 promoter.

This embodiment encompasses isolated or substantially purified nucleic acid compositions. An "isolated" or "purified" nucleic acid molecule, or biologically active portion thereof, is substantially free of other cellular material or culture medium when produced by recombinant techniques, or substantially free of chemical precursors or other chemicals when chemically synthesized. An "isolated" nucleic acid is substantially free of sequences (including protein encoding sequences) that naturally flank the nucleic acid (i.e., sequences located at the 5' and 3' ends of the nucleic acid) in the genomic DNA of the *Elaeis* species. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived.

Another aspect of the present disclosure contemplates a method for expressing a nucleotide sequence in a plant and/or plant cell, the method comprising introducing in a plant and/or plant cell or a parent of the plant or plant cell, a DNA construct, comprising a UEP1 promoter operably linked to a heterologous nucleotide sequence of interest.

As used herein, the term "construct" and/or "vector" and/or "plasmid" refers to a nucleic acid molecule capable of carrying another nucleic acid to which it has been linked or inserted. Particular vectors are those capable of expression of nucleic acids contained within. Vectors capable of directing the expression of genetic material to which they are operatively linked are referred to herein as "expression vectors." In general, expression vectors of utility in recombinant DNA techniques are often in the form of "plasmids" which refer generally to circular double stranded DNA loops which, in their vector form, are not bound to the chromosome. In the present specification, "plasmid" and "vector" are used interchangeably. In particular, the plasmid or vector comprises the UEP1 promoter and either a heterologous nucleotide sequence operably linked thereto or restriction endonuclease means to insert a heterologous nucleotide sequence in operable linkage to the UEP1 promoter. By "restriction endonuclease means" is meant one or more restriction endonuclease sites which can be used to linearize a covalently closed circular plasmid in order to re-ligate in the presence of a heterologous nucleotide sequence such that the heterologous nucleotide sequence is operably linked to the UEP1 promoter.

The term "genetic material" includes a "gene" which is used in its broadest sense and encompasses cDNA corresponding to the exons of a gene. Accordingly, reference herein to a "gene" is to be taken to include:—
  (i) a classical genomic gene consisting of transcriptional and/ or translational regulatory sequences and/or a coding region and/or non-translated sequences (i.e. introns, 5'- and 3'-untranslated sequences);

(ii) mRNA or cDNA corresponding to the coding regions (i.e. exons) and 5'- and 3-untranslated sequences of the gene; and/or
(iii) genetic material which when transcribed gives rise to mRNA or other RNA species or after translation gives rise to a peptide, polypeptide or protein.

The term "genetic material" and "gene" is also used to describe synthetic or fusion molecules encoding all or part of a functional product. The term "genetic material" also encompasses a gene or such molecules as RNAi, ssRNA, dsRNA and the like.

The genetic material may be in the form of a genetic construct comprising a gene or nucleic acid molecule to be introduced into a plant cell operably linked to a UEP1 promoter and optionally operably linked to various regulatory sequences.

The genetic material of the present disclosure may comprise a sequence of nucleotides or be complementary to a sequence of nucleotides which comprise one or more of the following: a promoter sequence, a 5' non-coding region, a cis-regulatory region such as a functional binding site for transcriptional regulatory protein or translational regulatory protein, an upstream activator sequence, an enhancer element, a silencer element, a TATA box motif, a CCAAT box motif, or an upstream open reading frame, transcriptional start site, translational start site, and/or nucleotide sequence which encodes a leader sequence.

The term "5' non-coding region" is used herein in its broadest context to include all nucleotide sequences which are derived from the upstream region of an expressible gene, other than those sequences which encode amino acid residues which comprise the polypeptide product of said gene, wherein the 5' non-coding region confers or activates or otherwise facilitates, at least in part, expression of the gene. The UEP1 promoter is contained within the 5' non-coding region of the genomic gene encoding the UEP. The nucleotide sequence of the 5' region of the UEP1 gene is set forth in SEQ ID NO:2 and the 5' end of SEQ ID NO:1.

The UEP1 promoter is constitutively expressed in *Elaeis* tissue and its expression was identified by screening the expression pattern of EST clones by using reverse northern analysis, northern analysis and DNA sequencing experiments which are further disclosed in Example 1. The amino acid sequence of the polypeptide encoded by the UEP1 gene (SEQ ID NO:3) is presented as SEQ ID NO:4. The 3' end of the UEP1 gene is presented in SEQ ID NO:5. In certain embodiments, the UEP1 promoter sequence directs expression of operably linked nucleotide sequences in all tissues. In *Elaeis* tissue, the UEP1 promoter may direct constitutive expression. However, the present disclosure extends to modified UEP1 promoters which have become fully or partially inducible.

Reference herein to a "promoter" is to be taken in its broadest context. A promoter is a short DNA sequence, usually upstream (5') to the relevant coding sequence, to which RNA polymerase binds before initiating transcription. This binding aligns the RNA polymerase so that transcription will initiate at a specific site. The nucleotide sequence of the promoter determines the nature of the enzyme that attaches to it and the rate of RNA synthesis. The RNA is processed to produce messenger RNA (mRNA) which serves as a template for translation of the RNA sequence into the amino acid sequence of the encoded polypeptide. The 5' non-translated leader sequence is a region of the mRNA upstream of the coding region that may play a role in initiation and translation of the mRNA. The 3' transcription termination/polyadenylation signal is a non-translated region downstream of the coding region that functions in the plant cells to cause termination of the RNA and the addition of polyadenylate nucleotides to the 3' end. Certain promoters are able to direct RNA synthesis at a higher rate than others. The term "promoter" as used herein includes the transcriptional regulatory sequences of a classical genomic gene, including the TATA box which is required for accurate transcription initiation, with or without a CCAAT box sequence and additional regulatory elements (i.e. upstream activating sequences, enhancers and silencers) which alter expression of genetic material in response to developmental and/or environmental stimuli, or in a tissue-specific or cell-type-specific manner. A UEP1 promoter is usually, but not necessarily, positioned upstream or 5', of genetic material, the expression of which it regulates. This is referred to as the promoter being operably linked to a particular nucleotide sequence.

In order to functionally express a gene in plant, the transgene must have a promoter that is recognized by RNA polymerase in plant cells. There are two major classes of promoter, constitutive and regulated (or inducible). Constitutive promoters direct expression in virtually all tissues and are largely, if not entirely, independent of environmental and developmental factors. As their expression is normally not conditioned by endogenous factors, constitutive promoters are usually active across species and even across kingdoms. Tissue-specific or development-stage-specific promoters (regulated) direct the expression of a gene in specific tissue(s) or at certain stages of development. For plants, promoter elements that are expressed or affect the expression of genes in the vascular system, photosynthetic tissues, tubers, roots and other vegetative organs, or seeds and other reproductive organs can be found in heterologous systems (e.g. distantly related species or even other kingdoms) but the most specificity is generally achieved with homologous promoters (i.e. from the same species, genus or family). This is probably because the coordinate expression of transcription factors is necessary for regulation of the promoter's activity.

Because promoters affect transcription both quantitatively and qualitatively, the success of gene transfer technologies, varying from basic research to crop improvement and biopharming, may depend on their efficacious selection and use (Potenza et al, *In Vitro Cell. Dev. Biol. Plant* 40:1-22, 2004). Plant promoters that are capable of driving high and constitutive expression of a particular transgene have become a valuable tool in plant genetic engineering. These promoters are required to select transgenic cells or plants that have a high level of production of the specific protein of interest. The high expression of a selectable marker is important to identify a non-transformed cell and to enable selection of a resistant transformant which will survive and generate into transgenic plant (Parveez, 1998, supra). This prevents non-transformant domination of the culture and promotes the growth of chimeric plants (Christou, *The Plant J.* 2:275-281, 1992; Ritala et al, *Plant Mol. Biol.* 24: 317-325, 1994). The high level expression of a reporter protein such as GUS, GFP and CAT in a plant cell can also be achieved by using constitutive promoters. Moreover, the use of constitutive promoters can be essential in the production of compounds that require ubiquitous activity in the plant and during all stages of plant development.

There are diverse spectra of constitutive promoters which are available to use in the genetic engineering of plants (Xiao et al, *Molecular Breeding,* 15:221-231, 2005). A commonly used example which results in the strong constitutive expression of a transgene in a plant is the CaMV35S promoter which originates from the cauliflower mosaic virus (Potenza et al, *In Vitro Cell. Dev. Biol. Plant* 40:1-22, 2004). Additionally, it has been reported that a number of widely used constitutive promoters include maize ubiquitin (Christensen and Quail, *Transgenic Research* 5:213-218, 1996), rice Actin 1 (McElroy et al, *Plant Cell.* 2:163-171, 1990) and maize derived Emu (Last et al, *Theor. Appl. Genet.*, 81:581-588, 1991).

As in other genetically engineered plants, constitutive promoters have previously been used to drive the expression of genes in transgenic oil palms. The promoters, Emu and Ubi1, were found to be the most efficient promoters in driving high level expression of foreign genes in oil palm plants (Chowdhury et al, *Plant Cell Rep.*, 16: 277-82, 1997). However, these promoters originated from unrelated plant species. Previous studies have shown that promoters can be more effective if isolated from the same species as the transgenic plant. McElroy et al, 1990 supra found, for example that β-glucuronidase (GUS) expression under the control of a rice actin promoter (Act1) in transformed rice protoplasts was approximately 6-fold greater than expression induced under the control of the maize Adh1 promoter.

The present disclosure includes isolated nucleic acid molecules comprising the promoter nucleotide sequence set forth in the 5' end of SEQ ID NO 1 or SEQ ID NO:2.

In the present context, the term "UEP1 promoter" is also used to describe a synthetic or fusion promoter molecule, or derivative thereof which confers, activates or enhances expression of genetic material.

The term "operably connected" or "operably linked" in the present context means placing a genetic material under the regulatory control of the UEP1 promoter which then controls expression of this material. The promoter is generally positioned 5' (upstream) to the genes which they control. As indicated above, in one embodiment, the UEP1 promoter functions constitutively.

The present disclosure extends to regulatory elements within the UEP1 promoter or added or incorporated therewith. In the context of this disclosure, the term "regulatory element" also refers to a sequence of NA, either, upstream (5') or downstream (3') to the coding sequence of the genetic materials to be expressed, which includes sequences which control the expression of the coding region by providing the recognition for RNA polymerase and/or other factors required for transcription to start at a particular site. An example of a regulatory element that provides for the recognition for RNA polymerase or other transcriptional factors to ensure initiation at a particular site is a promoter element. A promoter element comprises a core promoter element, responsible for the initiation of transcription, as well as other regulatory elements (as discussed elsewhere in this specification) that modify gene expression. It is to be understood that nucleotide sequences, located within introns or 3' of the coding region sequence also contribute to the regulation of expression of a coding region of interest. In the context of the present disclosure, a post-transcriptional regulatory element located 3' to the coding sequence may include elements that are active following transcription initiation, for example translational and transcriptional enhancers, translational and transcriptional repressors, and mRNA stability determinants.

The UEP1 promoter sequence, when assembled within a DNA construct such that the promoter is operably linked to a nucleotide sequence of interest, enables expression of the nucleotide sequence in the cells of a plant stably transformed with this DNA construct as well as progeny or relatives of these cells. As indicated above, the term "operably linked" is intended to mean that the transcription or translation of the heterologous nucleotide sequence is under the influence of the promoter sequence. "Operably linked" is also intended to mean the joining of two nucleotide sequences such that the coding sequence of each DNA fragment remains in the proper reading frame. In this manner, nucleotide sequences for the UEP1 promoter of the present disclosure are provided in DNA constructs along with the nucleotide sequence of interest, typically a heterologous nucleotide sequence, for expression in the plant of interest. The term "heterologous nucleotide sequence" is intended to mean a sequence that is not naturally operably linked with the UEP1 promoter sequence. While this nucleotide sequence is heterologous to the promoter sequence, it may be homologous or native; or heterologous or foreign, to the plant host. It is recognized that the UEP1 promoter of the present invention may be used with its native coding sequences to increase or decrease expression, thereby resulting in a change in phenotype of the transformed plant. For example, the UEP1 gene sequence or part thereof may be fused at the 5' or 3' end to another sequence.

Modifications of the isolated UEP1 promoter sequences of the present disclosure can provide for a range of expression of the heterologous nucleotide sequence. Fragments and variants of the UEP1 promoter sequences are also encompassed by the present disclosure. A "fragment" is intended to mean a portion of the promoter sequence. Fragments of a promoter sequence may retain biological activity and hence encompass fragments capable of driving inducible expression of an operably linked nucleotide sequence. Thus, for example, less than the entire promoter sequence disclosed herein may be utilized to drive expression of an operably linked nucleotide sequence of interest, such as a nucleotide sequence encoding a heterologous protein or an RNA species.

Those skilled in the art are able to determine whether such fragments decrease expression levels or alter the nature of expression, e.g. from constitutive to inducible expression. Alternatively, fragments of a promoter nucleotide sequence that is useful as hybridization probes, such as described below, may not retain this regulatory activity. Thus, fragments of a nucleotide sequence may range from at least about 20 nucleotides, about 50 nucleotides, about 100 nucleotides, about 500 nucleotides, about 1000 nucleotides and up to the full-length nucleotide sequence of the UEP1 promoter.

Thus, a fragment of a UEP1 promoter nucleotide sequence may comprise a biologically active portion or it may be a fragment that can be used as a hybridization probe or PCR primer to identify homolog promoters or to screen for the presence of the UEP1 promoter. A biologically active portion of the UEP1 promoter can be prepared by isolating a portion of the UEP1 promoter nucleotide sequence and assessing the activity of that portion of the UEP1 promoter.

The nucleotides of such fragments usually comprise the TATA recognition sequence of the particular promoter sequence. Such fragments may be obtained by use of restriction enzymes to cleave the naturally occurring promoter nucleotide sequence disclosed herein; by synthesizing a nucleotide sequence from the naturally occurring sequence of the promoter DNA sequence; or may be obtained through the use of PCR technology. See particularly, Mullis et al, *Methods Enzymol.* Vol. 55:335-350, 1987, and Erlich, ed. PCR Technology (Stockton Press, New York, 1989). Variants of these promoter fragments, such as those resulting from site-directed mutagenesis and a procedure such as DNA "shuffling", are also encompassed by the compositions of the embodiments. An "analog" of the regulatory elements of the embodiments includes any substitution, deletion, or addition to the sequence of a regulatory element provided that said analog maintains at least one regulatory property associated with the activity of the regulatory element of the embodiments.

The term "variants" is intended to mean sequences having substantial similarity with a promoter sequence disclosed herein. For nucleotide sequences, naturally occurring variants such as these can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis. Generally, variants of a particular nucleotide sequence of the embodiments will have at least 40%, 50%, 60%, 65%, 70%, 75%, 80%, 85%, 90%, 91%, 92%, 93%, 94%, to 95%, 96%, 97%, 98%, or 99% or more sequence identity to that particular nucleotide sequence as determined by sequence alignment programs described elsewhere herein using default parameters. Biologically active variants are also encompassed by the embodiments. Biologically active variants include, for example, the native promoter sequences of the embodiments having one or more nucleotide substitutions, deletions, or insertions. Promoter activity may be measured by using techniques such as Northern blot analysis, reporter activity measurements taken from transcriptional fusions, and the like. See, for example, Sambrook et al, (*Molecular Cloning: A Laboratory Manual* (2d ed., Cold Spring Harbor Laboratory Press, Cold Spring Harbor, N.Y., 1989), hereinafter "Sambrook," herein incorporated by reference. Alternatively, levels of a reporter gene such as green fluorescent protein (GFP) or the like produced under the control of a promoter fragment or variant can be measured. See, for example, U.S. Pat. No. 6,072,050.

Methods for mutagenesis and nucleotide sequence alterations are well known in the art. See, for example, Kunkel, *Proc. Natl. Acad. Sci. USA* 82:488-492, 1985; Kunkel et al, *Methods in Enzymol.* 54:367-382, 1987; U.S. Pat. No. 4,873, 192; Walker and Gaastra, eds., *Techniques in Molecular Biology*, MacMillan Publishing Company, New York, 1983 and the references cited therein. Variant promoter nucleotide sequences also encompass sequences derived from a mutagenic and recombinogenic procedure such as DNA shuffling. With such a procedure, one or more different promoter sequences can be manipulated to create a new promoter possessing the desired properties. In this manner, libraries of recombinant polynucleotides are generated from a population of related sequence polynucleotides comprising sequence regions that have substantial sequence identity and can be homologously recombined in vitro or in vivo. Strategies for such DNA shuffling are known in the art. See, for example, Stemmer, *Proc. Natl. Acad. Sci. USA* 91:10747-10751, 1994; Stemmer, *Nature* 370:389-391, 1994; Crameri et al, *Nature Biotech.* 15:436-438, 1997; Moore et al, *J. Mol. Biol.* 272: 336-347, 1997; Zhang et al, *Proc. Natl. Acad. Sci. USA* 94:4504-4509, 1997; Crameri et al, *Nature* 391:288-291, 1998; and U.S. Pat. Nos. 5,605,793 and 5,837,458.

The UEP1 promoter sequence of the present disclosure can be used to isolate corresponding sequences from other organisms, such as other plants, for example, other monocots. In this manner, methods such as PCR, hybridization, and the like can be used to identify such sequences based on their sequence homology to the sequence set forth herein. Sequences isolated based on their sequence identity to the entire UEP1 promoter sequence set forth herein or to fragments thereof are encompassed by the embodiments. The promoter regions of the present disclosure may be isolated from any plant, including, but not limited to corn (*Zea mays*), *Brassica* (*Brassica napus, Brassica rapa*), alfalfa (*Medicago sativa*), rice (*Oryza sativa*), rye (*Secale cereale*), sorghum (*Sorghum bicolor, Sorghum vulgare*), sunflower (*Helianthus annuus*), wheat (*Triticum aestivum*), soybean (*Glycine max*), tobacco (*Nicotiana tabacum*), potato (*Solarium tuberosum*), peanuts (*Arachis hypogaea*), cotton (*Gossypium hirsutum*), sweet potato (*Ipomoea batatus*), cassava (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), oats, barley, safflower, vegetables, ornamentals, and conifers.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook, 1989 supra. See also Innis et al, eds. *PCR Protocols: A Guide to Methods and Applications* (Academic Press, New York), 1990; Innis and Gelfand, eds. *PCR Strategies* (Academic Press, New York), 1995; and Innis and Gelfand, eds. *PCR Methods Manual* (Academic Press, New York), 1999. Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the UEP1 promoter sequence. Methods for preparation of probes for hybridization and for construction of cDNA and genomic libraries are generally known in the art and are disclosed in Sambrook, 1989 supra.

For example, the entire UEP1 promoter sequence disclosed herein, or one or more portions thereof, may be used as a probe capable of specifically hybridizing to corresponding (homolog or variant) UEP1 promoter sequences. To achieve specific hybridization under a variety of conditions, such probes include sequences that are unique among UEP1 promoter sequences and are generally at least about 10 nucleotides in length, including sequences of at least about 20 nucleotides in length including at least 30 nucleotides in length including large fragments or a full length promoter. Such probes may be used to amplify corresponding UEP1 promoter sequences from a chosen plant by PCR. This technique may be used to isolate additional coding sequences from a desired plant or as a diagnostic assay to determine the presence of coding sequences in a plant. Hybridization techniques include hybridization screening of plated DNA libraries (either plaques or colonies; see, for example, Sambrook supra). Hybridization of such sequences may be carried out under stringent conditions. "Stringent conditions" or "stringent hybridization conditions" are conditions under which a probe will hybridize to its target sequence to a detectably greater degree than to other sequences (e.g., at least two-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing).

Typically, stringent conditions will be those in which the salt concentration is less than about 1.5M Na ion, typically about 0.01 to 1.0M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% v/v formamide, 1M NaCl, 1% w/v SDS (sodium dodecyl sulphate) at 37° C., and a wash in 1× to 2×SSC (2×SSC=3.0 M NaCl/0.3 M trisodium citrate) at 50 to 55° C. Exemplary moderate stringency conditions include hybridization in 40 to 45% v/v formamide, 1.0M NaCl, 1% w/v SDS at 37° C., and a wash in 0.5× to 1×SSC at 55 to 60° C. Exemplary high stringency conditions include hybridization in 50% v/v formamide, 1M NaCl, 1% w/v SDS at 37° C., and a final wash in 0.1×SSC at 60 to 65° C. for at least 30 minutes. Duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the thermal melting point ($T_m$) can be approximated from the equation of Meinkoth and Wahl (1984) *Anal. Biochem*, Vol. 38:267-284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the Tm for the specific sequence and its complement at a defined ionic strength and pH. However, severely stringent conditions can utilize a hybridization and/or wash at 1, 2, 3, or 4° C. lower than the $T_m$; moderately stringent conditions can utilize a hybridization and/or wash at 6, 7, 8, 9, or 10° C. lower than the $T_m$; low stringency conditions can utilize a hybridization and/or wash at 11, 12, 13, 14, 15, or 20° C. lower than the $T_m$. Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen, *Laboratory Techniques in Biochemistry and Molecular Biology—Hybridization with Nucleic Acid Probes*, Part II Chapter 2 (Elsevier, New York), 1993; and Ausubel et al, eds. *Current Protocols in Molecular Biology*, Chapter 2 (Greene Publishing and Wiley-Interscience, New York), 1995, hereinafter "Ausubel". See also Sambrook, 1989 supra.

Thus, isolated sequences that have promoter activity and which hybridize under stringent conditions to the UEP1 promoter sequences disclosed herein, or to fragments thereof, are encompassed by the embodiments.

In general, sequences that have promoter activity and hybridize to the UEP1 promoter sequence disclosed herein have at least 40% to 50% homology, about 60%, 70%, 80%, 85%, 90%, 95% to 98% homology or more with the disclosed UEP1 promoter sequences. That is, the sequence similarity of sequences may range, sharing at least about 40% to 50%, about 60% to 70%, and about 80%, 85%, 90%, 95% to 98% sequence similarity. The following terms are used to describe the sequence relationships between two or more nucleic acids or polynucleotides: (a) "reference sequence", (b) "comparison window", (c) "sequence identity", (d) "percentage of sequence identity", and (e) "substantial identity".

As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller, *CABIOS* 4:11-17, 1988; the local homology algorithm of Smith et al, *Adv. Appl. Math.* 2:482, 1981; the homology alignment algorithm of Needleman and Wunsch, *J. Mal. Biol.* 48:443-453, 1970; the algorithm of Pearson and Lipman, *Proc. Natl. Acad. Sci.* 85:2444-2448, 1988; the algorithm of Karlin and Altschul, *Proc. Natl. Acad. Sci. USA* 872264, 1990, modified as in Karlin and Altschul, *Proc. Natl. Acad. Sci. USA* 90:5873-5877, 1993.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0); the ALIGN PLUS program (Version 3.0, copyright 1997): and GAP, BESTFIT, BLAST, FASTA, and TFASTA in the Wisconsin Genetics Software Package of Genetics Computer Group, Version 10 (available from Accelrys, 9685 Scranton Road, San Diego, Calif., 92121, USA). The scoring matrix used in Version 10 of the Wisconsin Genetics Software Package is BLOSUM62 (see Henikoff and Henikoff, *Proc. Natl. Acad. Sci. USA* 89:10915, 1989).

Alignments using these programs can be performed using the default parameters. The CLUSTAL program is well described by Higgins et al, *Gene* 73:237-244, 1988; Higgins et al, *CABIOS* 5:151-153, 1989; Corpet et al, *Nucleic Acids Res.*—Vol. 6:10881-90, 1988; Huang et al, *CABIOS* 8:155-65, 1992; and Pearson et al, *Meth. Mol. Biol.* 24:307-331, 1994. The ALIGN and the ALIGN PLUS programs are based on the algorithm of Myers and Miller (1988) supra. A PAM 120 weight residue table, a gap length penalty of 12, and a gap penalty of four can be used with the ALIGN program when comparing amino acid sequences. The BLAST programs of Altschul et al, *J. Mol. Biol.* 215:403, 1990 are based on the algorithm of Karlin and Altschul 1990 supra. BLAST nucleotide searches can be performed with the BLASTN program, score=100, word length=12, to obtain nucleotide sequences homologous to a nucleotide sequence encoding a protein of the embodiments. BLAST protein searches can be performed with the BLASTX program, score=50, word length=3, to obtain amino acid sequences homologous to a protein or polypeptide of the embodiments. To obtain gapped alignments for comparison purposes, Gapped BLAST (in BLAST 2.0) can be utilized as described in Altschul et al, *Nucleic Acids Res.* 25:3389, 1997. Alternatively, PSI-BLAST (in BLAST 2.0) can be used to perform an iterated search that detects distant relationships between molecules. See Altschul et al 1997 supra. When utilizing BLAST, Gapped BLAST, PSI-BLAST, the default parameters of the respective programs (e.g., BLASTN for nucleotide sequences, BLASTX for proteins) can be used. See the web site for the National Center for Biotechnology Information on the World Wide Web. Alignment may also be performed manually by inspection.

Unless otherwise stated, sequence identity/similarity values provided herein refer to the value obtained using the VectorNTI program with default parameters, or any equivalent program. By "equivalent program" is intended any sequence comparison program that, for any two sequences in question, generates an alignment having identical nucleotide or amino acid residue matches and an identical percent sequence identity when compared to the corresponding alignment generated by VectorNTI (Invitrogen).

As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The term "substantial identity" of polynucleotide sequences means that a polynucleotide comprises a sequence that has at least 70% sequence identity, at least 80%, at least 90%, or at least 95%, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 60%, 70%, 80%, 90%, and at least 95%.

Another indication that nucleotide sequences are substantially identical is if two molecules hybridize to each other under stringent conditions. Generally, stringent conditions are selected to be about 5° C. lower than the $T_m$ for the specific sequence at a defined ionic strength and pH. However, stringent conditions encompass temperatures in the range of about 1° C. to about 20° C. lower than the $T_m$, depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

The UEP1 promoter sequence disclosed herein, as well as variants and fragments thereof, are useful for genetic engineering of plants, e.g. for the production of a transformed or transgenic plant, to express a phenotype of interest. As used herein, the terms "transformed plant" and "genetically modified plant" refer to a plant that comprises within its genome a heterologous polynucleotide. It includes an initially modified plant as well as its progeny which carry the same genetic modification. Generally, the heterologous polynucleotide is stably integrated within the genome of a genetically modified or transformed plant such that the polynucleotide is passed on to successive generations. The heterologous polynucleotide may be integrated into the genome alone or as part of a recombinant DNA construct. It is to be understood that as used herein the terms "genetically modified" and "transgenic" includes any cell, cell line, callus, tissue, plant part, or plant the genotype of which has been altered by the presence of heterologous nucleic acid including those transgenics initially so altered as well as those created by sexual crosses or asexual propagation from the initial transgenic. "Genetically modified" and "transgenic" as used herein do not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation. A transgenic "event" is produced by transformation of plant cells with a heterologous DNA construct, including a nucleic acid DNA construct that comprises a transgene of interest, the regeneration of a population of plants resulting from the insertion of the transgene into the genome of the plant, and selection of a particular plant characterized by insertion into a particular genome location. An event is characterized phenotypically by the expression of the transgene. At the genetic level, an event is part of the genetic makeup of a plant. The term "event" also refers to progeny produced by a sexual outcross between the transformant and another variety that include the heterologous DNA.

As used herein, the term "plant" includes reference to whole plants, plant organs (e.g., leaves, stems, roots, etc.), seeds, plant cells, and progeny of same. Parts of transgenic plants are to be understood within the scope of the embodiments to comprise, for example, plant cells, protoplasts, tissues, callus, embryos as well as flowers, stems, fruits, ovules, leaves, or roots originating in transgenic plants or their progeny previously transformed with a DNA molecule of the embodiments, and therefore consisting at least in part of transgenic cells. As used herein, the term "plant cell" includes, without limitation, seeds suspension cultures, embryos, meristematic regions, callus tissue, leaves, roots, shoots, gametophytes, sporophytes, pollen, and microspores. The class of plants that can be used in the methods disclosed herein is generally as broad as the class of higher plants amenable to transformation techniques, including both monocotyledonous and dicotyledonous plants.

The UEP1 promoter sequence disclosed herein is useful in regulating expression of any heterologous nucleotide sequence in a host plant. Thus, the heterologous nucleotide sequence operably linked to the promoters disclosed herein may be a structural gene encoding a protein of interest. Genes of interest are reflective of the commercial markets and interests of those involved in the development of the crop. Crops and markets of interest change, and as developing nations open up world markets, new crops and technologies will emerge also. In addition, as our understanding of agronomic traits and characteristics such as yield and heterosis increase, the choice of genes for transformation will change accordingly. General categories of genes of interest for the embodiments include, for example, those genes involved in information, such as zinc fingers, those involved in communication, such as kinases, and those involved in housekeeping, such as heat shock proteins. More specific categories of transgenes, for example, include genes encoding proteins conferring resistance to abiotic stress, such as drought, temperature, salinity, and toxins such as pesticides and herbicides, or to biotic stress, such as attacks by fungi, viruses, bacteria, insects, and nematodes, and development of diseases associated with these organisms. Various changes in phenotype are of interest including modifying expression of a gene in a plant, altering a plant's pathogen or insect defense mechanism, increasing the plant's tolerance to herbicides, altering plant development to respond to environmental stress, and the like. The results can be achieved by providing expression of heterologous or increased expression of endogenous products in plants. Alternatively, the results can be achieved by providing for a reduction of expression of one or more endogenous products, particularly enzymes, transporters, or cofactors, or affecting nutrients uptake in the plant. These changes result in a change in phenotype of the transformed plant. It is recognized that any gene of interest can be operably linked to the promoter sequences of the embodiments and expressed in a plant.

A DNA construct comprising one of these genes of interest can be used with transformation techniques, such as those described below, to create disease or insect resistance in susceptible plant phenotypes or to enhance disease or insect resistance in resistant plant phenotypes. Accordingly, the embodiments encompass methods that are directed to protecting plants against fungal pathogens, bacteria, viruses, nematodes, insects, and the like. By "disease resistance" is intended that the plants avoid the harmful symptoms that are the outcome of the plant-pathogen interactions.

Disease resistance and insect resistance genes such as lysozymes, cecropins, maganins, or thionins for antibacterial protection, or the pathogenesis-related (PR) proteins such as glucanases and chitinases for anti-fungal protection, or *Bacillus thuringiensis* endotoxins, protease inhibitors, collagenases, lectins, and glycosidases for controlling nematodes or insects are all examples of useful gene products.

Genes encoding disease resistance traits include detoxification genes, such as against fumonisin (U.S. Pat. No. 5,792,931) avirulence (avr) and disease resistance (R) genes (Jones et al. (1994) *Science* 266:789; Martin et al. (1993) *Science* 262:1432; Mindrinos et al. (1994) *Cell* 78:1089); and the like. The UEP1 promoter of the embodiments may be used to express disease resistance genes in a constitutive manner to prevent disease pathogens that typically infect plants.

The UEP1 promoter of the present disclosure may also be used to express genes in a root-preferred manner which may include, for example, insect resistance genes directed to those insects which primarily feed on the roots. Such insect resistance genes may encode resistance to pests that have great yield drag such as various species of rootworms, cutworms, and the like. Such genes include, for example, *Bacillus thuringiensis* toxic protein genes (U.S. Pat. Nos. 5,366,892; 5,747,450; 5,737,514; 5,723,756; 5,593,881; and Geiser et al, *Gene* 48:109, 1986); lectins (Van Damme et al, *Plant Mol. Biol.* 24:825, 1994); and the like. Herbicide resistance traits may be introduced into plants by genes coding for resistance to herbicides that act to inhibit the action of acetolactate synthase (ALS), in particular the sulfonylurea-type herbicides (e.g., the acetolactate synthase (ALS) gene containing mutations leading to such resistance, in particular the S4 and/or Hra mutations), genes coding for resistance to herbicides that act to inhibit action of glutamine synthase, such as phosphinothricin or basta, or other such genes known in the art. The bar gene encodes resistance to the herbicide basta, the nptll gene encodes resistance to the antibiotics kanamycin and geneticin, and the ALS gene encodes resistance to the herbicide chlorsulfuron.

Commercial traits can also be encoded on a gene or genes that could increase for example, starch for ethanol production, or provide expression of proteins. Another important commercial use of transformed plants is the production of polymers and bioplastics such as described in U.S. Pat. No. 5,602,321. Genes such as β-Ketothiolase, PHBase (polyhydroxyburyrate synthase), and acetoacetyl-CoA reductase (see Schubert et al, *J. Bacterial.* 170:5837-5847, 1988) facilitate expression of polyhyroxyalkanoates (PHAs).

Agronomically important traits that affect quality of palm oil products, such as levels and types of oils, saturated and unsaturated, quality and quantity of essential amino acids, levels of cellulose, starch, and protein content can be genetically altered using the methods of the present disclosure. Modifications include increasing content of oleic acid, saturated and unsaturated oils, increasing levels of lysine and sulfur, providing essential amino acids, and modifying starch.

Exogenous products include plant enzymes and products as well as those from other sources including prokaryotes and other eukaryotes. Such products include enzymes, cofactors, hormones, and the like.

Examples of other applicable genes and their associated phenotype include the gene that encodes viral coat protein and/or RNA, or other viral or plant genes that confer viral resistance; genes that confer fungal resistance; genes that confer insect resistance; genes that promote yield improvement; and genes that provide for resistance to stress, such as dehydration resulting from heat and salinity, toxic metal or trace elements, or the like.

The heterologous nucleotide sequence operably linked to the UEP1 promoter and its related biologically active fragments or variants disclosed herein may be an antisense sequence for a targeted gene. The terminology "antisense DNA nucleotide sequence" is intended to mean a sequence that is in inverse orientation to the 5'-to-3' normal orientation of that nucleotide sequence. When delivered into a plant cell, expression of the antisense DNA sequence prevents normal expression of the DNA nucleotide sequence for the targeted gene. The antisense nucleotide sequence encodes an RNA transcript that is complementary to and capable of hybridizing to the endogenous messenger RNA (mRNA) produced by transcription of the DNA nucleotide sequence for the targeted gene. In this case, production of the native protein encoded by the targeted gene is inhibited to achieve a desired phenotypic response. Modifications of the antisense sequences may be made as long as the sequences hybridize to and interfere with expression of the corresponding mRNA. In this manner, antisense constructions having 70%, 80%, 85% sequence identity to the corresponding antisense sequences may be used. Furthermore, portions of the antisense nucleotides may be used to disrupt the expression of the target gene. Generally, sequences of at least 50 nucleotides, 100 nucleotides, 200 nucleotides, or greater may be used. Thus, the promoter sequences disclosed herein may be operably linked to antisense DNA sequences to reduce or inhibit expression of a native protein in the plant. "RNAi" refers to a series of related techniques to reduce the expression of genes (See for example U.S. Pat. No. 6,506,559). Older techniques referred to by other names are now thought to rely on the same mechanism, but are given different names in the literature. These include "antisense inhibition," the production of antisense RNA transcripts capable of suppressing the expression of the target protein, and "co-suppression" or "sense-suppression," which refer to the production of sense RNA transcripts capable of suppressing the expression of identical or substantially similar foreign or endogenous genes (U.S. Pat. No. 5,231,020, incorporated herein by reference). Such techniques rely on the use of constructs resulting in the accumulation of double stranded RNA with one strand complementary to the target gene to be silenced. The UEP1 promoter sequence of the embodiments, and its related biologically active fragments or variants disclosed herein, may be used to drive expression of constructs that will result in RNA interference including microRNAs and siRNAs.

In one embodiment of the present disclosure, DNA constructs comprise a transcriptional initiation region comprising one of the promoter nucleotide sequences disclosed herein, or variants or fragments thereof, operably linked to a heterologous nucleotide sequence whose expression is to be controlled by the inducible promoter of the embodiments. Such a DNA construct is provided with a plurality of restriction sites for insertion of the nucleotide sequence to be under the transcriptional regulation of the regulatory regions. The DNA construct may additionally contain selectable marker genes.

The DNA construct includes in the 5'-3' direction of transcription, a UEP1 promoter, a heterologous nucleotide sequence of interest (or means for insertion of such a heterologous sequence), a translational termination region and, optionally, a transcriptional termination region functional in the host organism. The regulatory regions other than the UEP1 promoter (i.e., transcriptional regulatory regions, and translational termination regions) and/or the heterologous polynucleotide of the embodiments may be native/heterologous to the host cell or to each other. As used herein, "heterologous" in reference to a sequence is a sequence that originates from a species other than *Elaeis*, or, if from *Elaeis* species, is substantially modified from its native form in composition and/or genomic locus by deliberate human intervention. For example, a promoter operably linked to a heterologous polynucleotide is from *Elaeis* species different from the species from which the polynucleotide was derived, or, if from the same/analogous *Elaeis* species, one or both are substantially modified from their original form and/or genomic locus, or the promoter is not the native promoter for the operably linked polynucleotide.

The optionally included termination region may be native with the transcriptional initiation region, may be native with the operably linked polynucleotide of interest, may be native with the plant host, or may be derived from another source (i.e., foreign or heterologous) to the promoter, the polynucleotide of interest, the host, or any combination thereof. Convenient termination regions are available from the Ti-plasmid of *A. tumefaciens*, such as the octopine synthase and nopaline synthase termination regions.

The DNA construct comprising a promoter sequence of the embodiments operably linked to a heterologous nucleotide sequence may also contain at least one additional nucleotide sequence for a gene to be co-transformed into the organism. Alternatively, the additional sequence(s) can be provided on another DNA construct.

Where appropriate, the heterologous nucleotide sequence whose expression is to be under the control of the UEP1 promoter and any additional nucleotide sequence(s) may be optimized for increased expression in the transformed plant. That is, these nucleotide sequences can be synthesized using plant preferred codons for improved expression. Methods are available in the art for synthesizing plant-preferred nucleotide sequences. See, for example, U.S. Pat. Nos. 5,380,831 and 5,436,391, and Murray et al. (1989) *Nucleic Acids Res.* 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the heterologous nucleotide sequence may be adjusted to levels average for a given cellular host, as calculated by reference to known genes expressed in the host cell. When possible, the sequence is modified to avoid predicted hairpin secondary mRNA structures.

The DNA constructs may additionally contain 5' leader sequences. Such leader sequences can act to enhance translation.

The DNA constructs of the embodiments can also include further enhancers, either translation or transcription enhancers, as may be required. These enhancer regions are well known to persons skilled in the art, and can include the ATG initiation codon and adjacent sequences. The initiation codon must be in phase with the reading frame of the coding sequence to ensure translation of the entire sequence. The translation control signals and initiation codons can be from a variety of origins, both natural and synthetic. Translational initiation regions may be provided from the source of the transcriptional initiation region, or from the structural gene. The sequence can also be derived from the regulatory element selected to express the gene, and can be specifically modified so as to increase translation of the mRNA. It is recognized that to increase transcription levels enhancers may be utilized in combination with the promoter regions of the embodiments. Enhancers are known in the art and include the SV40 enhancer region, the 35S enhancer element, and the like.

In preparing the DNA construct, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites. Restriction sites may be added or removed, superfluous DNA may be removed, or other modifications of the like may be made to the sequences of the embodiments. For this purpose, in vitro mutagenesis, primer repair, restriction, annealing, re-substitutions, for example, transitions and transversions, may be involved. Reporter genes or selectable marker genes may be included in the DNA constructs. Examples of suitable reporter genes known in the art can be found in, for example, Jefferson et al. In Plant Molecular Biology Manual, ed. Gelvin et al. (Kluwer Academic Publishers), pp. 1-33, 1991; DeWet et al, *Mol. Cell. Biol.* 7:725-737, 1987; Goff et al, *EMBO J.* 0:2517-2522, 1990; Kain et al, *BioTechniques* 79:650-655, 1995; and Chiu et al, *Current Biology* 6:325-330, 1996.

Selectable marker genes for selection of transformed cells or tissues can include genes that confer antibiotic resistance or resistance to herbicides. Examples of suitable selectable marker genes include, but are not limited to, genes encoding resistance to chloramphenicol (Herrera Estrella et al, *EMBO J.* 2:987-992, 1983); methotrexate (Herrera Estrella et al, *Nature* 303:209-213, 1983; Meijer et al, *Plant Mol. Biol.* 16:807-820, 1991); hygromycin (Waldron et al, *Plant Mol. Biol.* 5:103-108, 1985; Zhijian et al, *Plant Science* 708:219-227, 1995); streptomycin (Jones et al, *Mol. Gen. Genet.* 270: 86-91, 1987); spectinomycin (Bretagne-Sagnard et al, *Transgenic Res.* 5:131-137, 1996); bleomycin (Hille et al, *Plant Mol. Biol.* 7:171-176, 1990); sulfonamide (Guerineau et al, *Plant Mol. Biol.* 75:127-136, 1990); bromoxynil (Stalker et al, *Science* 242:419-423, 1988); glyphosate (Shaw et al, *Science* 233:478-481, 1986); phosphinothricin (DeBlock et al, *EMBO J.* 6:2513-2518, 1987).

Other genes that could serve utility in the recovery of transgenic events but might not be required in the final product would include, but are not limited to, examples such as GUS (b-glucuronidase; Jefferson, *Plant Mol. Biol. Rep.* 5:387, 1987 (green fluorescent protein; Chalfie et al, *Science* 263:802, 1994), luciferase (Riggs et al, *Nucleic Acids Res.* 75(19):8115, 1987 and Luehrsen et al, *Methods Enzymol.* 276:397-414, 1992), and the maize genes encoding for anthocyanin production (Ludwig et al, *Science* 247:449, 1990).

The nucleic acid molecules of the embodiments are useful in methods directed to expressing a nucleotide sequence in a plant. This may be accomplished by transforming a plant cell of interest with a DNA construct comprising a promoter identified herein, operably linked to a heterologous nucleotide sequence, and regenerating a stably transformed plant from said plant cell. The methods of the embodiments are also directed to inducibly expressing a nucleotide sequence in a plant. Those methods comprise transforming a plant cell with a DNA construct comprising a promoter identified herein that initiates transcription in a plant cell in an inducible manner, operably linked to a heterologous nucleotide sequence, regenerating a transformed plant from said plant cell, and subjecting the plant to the required stimulus to induce expression. The DNA construct comprising the particular promoter sequence of the embodiments operably linked to a nucleotide sequence of interest can be used to transform any plant. In this manner, genetically modified, i.e. transgenic or transformed, plants, plant cells, plant tissue, seed, root, and the like can be obtained.

Plant species suitable for genetic manipulation other than *Elaeis* sp. include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), oats (*Avena* spp.), sunflower (*Helianthus annuus*), safflower (*Carthamus tinctorius*), wheat (*Triticum aestivum*), barley (*Hordeum* spp.), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), onion (*Allium* spp.), dates (*Phoenix* spp.), vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers that may be employed in practicing the embodiments include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*).

As used herein, "vector" refers to a DNA molecule such as a plasmid, cosmid, or bacterial phage for introducing a nucleotide construct, for example, an expression cassette, into a host cell. Cloning vectors typically contain one or a small number of restriction endonuclease recognition sites at which foreign DNA sequences can be inserted in a determinable fashion without loss of essential biological function of the vector, as well as a marker gene that is suitable for use in the identification and selection of cells transformed with the cloning vector. Marker genes typically include genes that provide tetracycline resistance, hygromycin resistance, or ampicillin resistance.

The methods of the present disclosure involve introducing a nucleotide construct into a plant. As used herein "introducing" is intended to mean presenting to the plant the nucleotide construct in such a manner that the construct gains access to the interior of a cell of the plant. The methods of the embodiments do not depend on a particular method for introducing a nucleotide construct to a plant, only that the nucleotide construct gains access to the interior of at least one cell of the plant. Methods for introducing nucleotide constructs into plants are known in the art including, but not limited to, stable transformation methods, transient transformation methods, and virus-mediated methods. A "stable transformation" is one in which the nucleotide construct introduced into a plant integrates into the genome of the plant and is capable of being inherited by progeny thereof. "Transient transformation" means that a nucleotide construct introduced into a plant does not integrate into the genome of the plant. The nucleotide constructs of the embodiments may be introduced into plants by contacting plants with a virus or viral nucleic acids. Generally, such methods involve incorporating a nucleotide construct of the embodiments within a viral DNA or RNA molecule. Methods for introducing nucleotide constructs into plants and expressing a protein encoded therein, involving viral DNA or RNA molecules, are known in the art. See, for example, U.S. Pat. Nos. 5,889,191, 5,889,190, 5,866,785, 5,589,367, and 5,316,931; herein incorporated by reference.

Transformation protocols as well as protocols for introducing nucleotide sequences into plants may vary depending on the type of plant or plant cell, i.e., monocotyledon or dicotyledon, targeted for transformation. Suitable methods of introducing nucleotide sequences into plant cells and subsequent insertion into the plant genome include microinjection (Crossway et al. (1986) *Biotechniques* 4:320-334), electroporation (Riggs et al. (1986) *Proc. Natl. Acad. Sci. USA* 83:5602-5606), *Agrobacterium*-mediated transformation (U.S. Pat. Nos. 5,981,840 and 5,563,055), direct gene transfer (Paszkowski et al, *EMBO J.* 3:2717-2722, 1984), and ballistic particle acceleration (see, for example, U.S. Pat. Nos. 4,945, 050; 5,879,918; 5,886,244; 5,932,782; Tomes et al, In Plant Cell, Tissue, and Organ Culture: Fundamental Methods, ed. Gamborg and Phillips (Springer-Verlag, Berlin), 1995; and McCabe et al, *Biotechnology* 6:923-926, 1988).

The cells that have been transformed may be grown into plants in accordance with conventional ways. See, for example, McCormick et al, *Plant Cell Reports* 5:81-84, 1986. These plants may then be grown, and crossed with the same transformed strain or different strains, and the resulting hybrid which expresses the desired phenotypic characteristic. Two or more generations may be grown to ensure that inducible expression of the desired phenotypic characteristic is stably maintained and inherited and then seeds or plantlets harvested to ensure expression of the desired phenotypic characteristic has been achieved. Thus as used herein, "transformed seeds" or "transformed plants" refers to seeds and plants that contain the nucleotide construct stably integrated into the plant genome.

There are a variety of methods for the regeneration of plants from plant tissue. The particular method of regeneration will depend on the starting plant tissue and the particular plant species to be regenerated. The regeneration, development and cultivation of plants from single plant protoplast transformants or from various transformed explants is well known in the art (Weissbach and Weissbach, *In: Methods for Plant Molecular Biology*, (Eds.), Academic Press, Inc., San Diego, Calif., 1988). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil. In one embodiment, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the embodiments containing a desired polypeptide is cultivated using methods well known to one skilled in the art.

The present disclosure provides vectors, cells, and plants comprising the UEP1 promoter operably linked to a heterologous DNA sequence. The UEP1 promoter can also be used to screen for agonists and antagonists of the UEP1 promoter. For example, a reporter gene can be operably linked to a UEP1 promoter and expressed as a transgene in a plant. Compounds to be tested are added and reporter gene expression is measured to determine the effect on promoter activity.

The present invention is further described in the following non-limiting Examples.

Example 1

Identifying a Constitutive Gene from an Oil Palm

Isolation of Total RNA

Total RNA was isolated from oil palm green leaves using the method as described by Zeng and Yang, *Plant. Mol. Biol. Rep.* 20:417a-417e, 2002.

Reverse Northern Analysis

Reverse northern analysis were performed according to the manufacturer's instructions (Bio-Dot® Microfiltration Apparatus, BIO-RAD). Wells of the dot blot were rinsed with 300 µl 2× buffered Saline Sodium-Citrate (SSC) (3M NaCl, 300 mM tri-sodium citrate, pH 7.0). About 200 µg of the amplicons was added to 0.4N NaOH. This mixture was then denatured by boiling for 10 min and immediately chilled on ice. About 100 µl of the preparation were loaded into the wells and aspirated through under vacuum. The wells were rinsed twice with 300 µl 2×SSC, sucked through the manifold under vacuum and briefly air-dried. The cDNA from oil palm tissues was prepared by reverse transcription of 3 µg total RNA according to the First Strand cDNA synthesis kit (Invitrogen). The membrane was UV crossed-link and probed with $[\alpha\text{-}^{32}P]$ cDNA produced according to the Megaprime™ DNA Labeling System manual (Amersham Life Science). Hybridization was carried out with standard reagents, according to standard techniques (Sambrook et al 1989, supra). Blots were exposed to Kodak XAR-5 film from 12 hours to 3 days.

Northern Analysis

About 15 µg of total RNA from various oil palm tissues was denatured in RNA loading buffer (50% formamide, 17% formaldehyde, 1×MOPS, 5% glycerol, 2.5% bromophenol blue). The mixture was denatured by heating the sample for 10 minutes at 65° C. followed by immediate cooling. Denatured total RNA was separated on 1% w/v formaldehyde gel using 1×MOPS Buffer (pH 7.0) as electrophoresis buffer. Transfer to nylon membrane (Hybond N+Amersham) was carried out using the capillary transfer method. Prehybridization and hybridization were carried out in the same solution. Prehybridization was carried out in a hybridization bottle (FHB11, Techne) containing 30 ml hybridization solution (5×SSC, 5×Denhardts, 0.5% w/v SDS and 100 µg/ml denatured herring sperm DNA). The prehybridization was carried out at 65° C. for at least 2 hours in Hybridiser HB-1D (Techne) hybridization oven. After prehybridization, the denatured labeled DNA probe was pipetted directly into the hybridization buffer without touching the membrane. The hybridization was performed at 65° C. overnight. After the hybridization was complete, membranes were removed from the bottle and washed in 1×SSC, 0.1% w/v SDS for 15 minutes at room temperature. The membranes were then washed twice for 30 minutes at 65° C. in 0.1×SSC and 0.1% w/v SDS. After washing, the membranes were placed in an autoradiography cassette and exposed to X-ray film (Kodak) with an intensifying screen at −80° C. for a week.

DNA Sequencing for Clone Verification

Plasmid DNA was prepared using the Plasmid Mini Preparation Kit (QIAGEN) according to the manufacturer's instructions. Although the identity of the clone was known, the sequence was verified and analyzed. Representative clones were sequenced using an automated DNA sequencer (ABI PRISM Model 377 Version 3.4). Analysis of DNA sequences was carried out using the VectorNTI software (Invitrogen). The analysis included the removal of unreadable and vector sequences, sequence alignment, ORF identification and contig-analysis and assembly. DNA and protein homology searches were performed against the GenBank databases using BLAST 2.0 (Altschul et al., 1997, supra).

Figure 2:
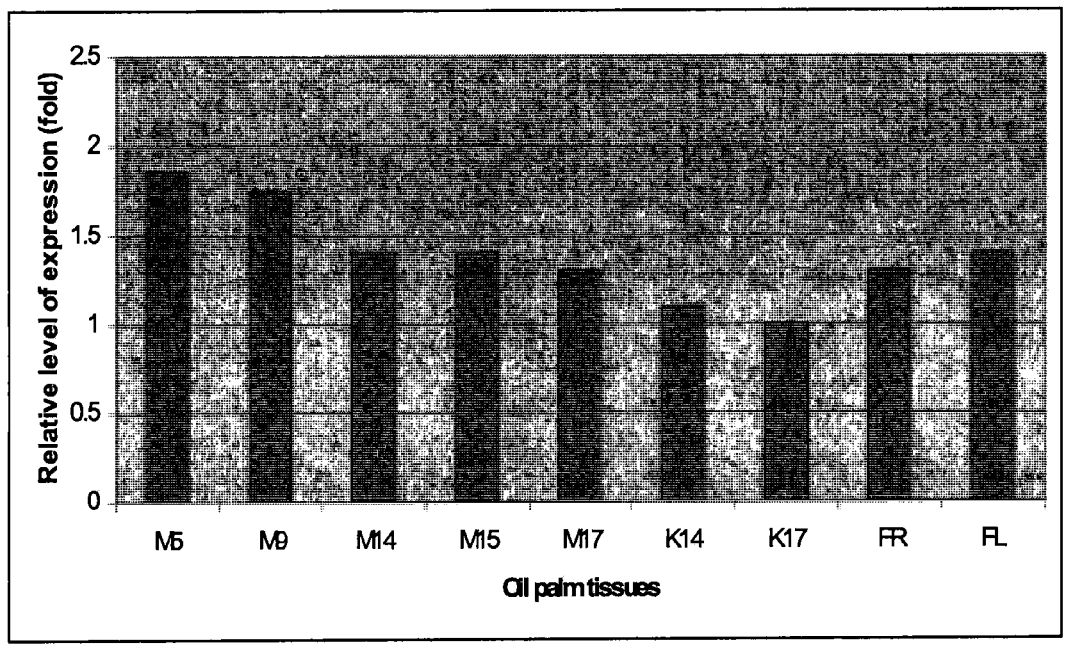
FIG. 2 is a graphical representation of the expression of pOPSFB-1301 cDNA in various tissues of oil palm through reverse northern analysis. The membranes was hybridized with first strand cDNA probe from A) mesocarp 5 WAA, B) mesocarp 9 WAA, C) mesocarp 12 WAA, D) mesocarp 15 WAA, E) mesocarp 17 WAA, F) kernel 14 WAA, G) kernel 17 WAA, H) frond and I) flower. Blue and red arrows indicate location of pOPSFB-1301 cDNA clone and ribosomal DNA, respectively.
Figure 3:
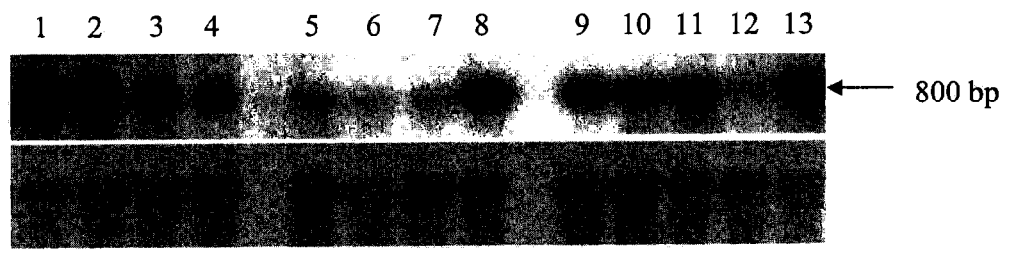
FIG. 3 is a photographic representation of a northern blot analysis for pOP-SFB1301 cDNA (a). Each lane contained 15 ug of total RNA prepared from different tissues of oil palm. Lane 1-4: Mesocarp at 5, 9, 15, 19 WAA, lane 5-7: kernel at 12, 14, 17 WAA, lane 8: stem (shoot tips), lane 9: young leaf, lane 10: flower, lane 11: root (from plantlet), lane 12: green leaf, lane 13: embryoid. Equal loading of RNA was verified with 28S ribosomal DNA (b). Arrow indicates the size of transcript.

The gene was identified through screening the expression pattern of 73 EST clones by using reverse northern analysis (FIG. 1). A cDNA clone, namely pOPSFB1301 which encoded ubiquitin extension protein (UEP1) gene showed the presence of strong signal in all tissues tested. The gene was expressed in all tissues tested with ranged of about 1.0-1.8 fold, with the highest expression was detected in mesocarp at week 5 (FIG. 2). The constitutive status of this gene was further validated using northern analysis. Results indicated that a transcript with size of about 0.8 kb was detected in total RNA of various oil palm tissues including mesocarps, kernels, frond, young leaf, embryoid, root, flower and stem, but with albeit slight of variation in RNA levels. The results obtained from the northern analysis also correlate to the reverse northern analysis.

Detailed sequence analysis showed that UEP1 gene encodes a polypeptide consisting of 76 acid amino residues of ubiquitin fused to a C-terminal extension. This extension is predicted to be 80 amino acids and was identified as small subunit ribosomal protein S27a. A comparison of pOPSFB-1301 cDNA sequence to entries in GeneBank revealed that this gene is related to its homologous counterparts from *Arabidopsis*, potato, barley, tomato, human and rat. The analysis showed that the domains are highly conserved amongst plant and non-plant species.

Example 2

Isolation of the Constitutive Promoter

Isolation of Total DNA

Extraction of genomic DNA was carried out according to Doyle and Doyle, *Phytochemical Bulletin* 19: 11-15, 1987.

Genome Walking

Pools of uncloned, adaptor-ligated genomic DNA fragments, which are referred to as GenomeWalker "libraries" were constructed. This technique was carried out according to the manufacturer's protocol. Four blunt-end digestions were performed using Dra1, EcoRV, PvuII and Ssp1 restriction enzymes. The digested DNA was purified and ligated with the GenomeWalker Adaptors. The 50 µl of primary and secondary PCR reactions consisted of 37.8 µl dH20, 5 µl 10× Tth PCR Reaction Buffer, 1 µl 10 mM dNTP, 2.20 Mg(OAc)$_2$, 1 µl 10 µM AP1, 1 µM 10 mM UEP1-1 or UEP1-2 primer and 1 µl Advantage Genomic Polymerase Mix. The PCR parameters for cycling of the first PCR reaction was performed as followed: 7 cycles of 94° C.: 25 sec, 72° C.; 3 min, 32 cycles of 94° C.; 25 sec, 67° C.; 3 min and 67° C.; 7 min. Second PCR parameters were performed as above but the cycles were reduced to 5 and 20 cycles, respectively.

Cloning the DNA Fragment

The PCR product was analyzed by agarose gel electrophoreses and the fragment obtained was purified using the QIAquick Gel Extraction Kit (QIAGEN®) as described in the manufacturer's manual. The purified PCR product was ligated into the pCRII-TOPO vector (TOPO TA Cloning Kit, Invitrogen Life Technologies) for further manipulation. Ligation reactions were carried out in mixtures of 3 µl (about 30 ng) of purified PCR product, 1 µl salt solution (1.2M NaCl, 0.06M MgCl2) and 1 µl (10 ng) vector plasmid. Sterilized water was added to the final volume of 6 µl. The mixture was incubated at room temperature for 5 to 10 minutes. The mixture was then cloned into One Shot® Chemically Competent *E. coli* according to the manufacturer's instructions.

DNA Sequencing for Clone Verification

Plasmid DNA was prepared using Plasmid Mini Preparation Kit (QIAGEN) according to the manufacturer's protocol. Representative clones were sequenced using an automated DNA sequencer (ABI PRISM Model 377 Version 3.4). Analysis of DNA sequences was carried out using VectorNTI software (Invitrogen). The analysis included the removal of unreadable and vector sequences, sequence alignment, ORF identification and contig-analysis and assembly. DNA and protein homology was investigated by using the GenBank databases and by using BLAST 2.0 (Altschul et al., 1997, supra). Prediction of the putative location of transcription start sites (TSS) was carried out using the Softberry database. Identification for cis acting regulatory elements was performed using a MOTIF search on publicly accessible databases. These databases include Softberry (available on the worldwide web at softberry.com/berry.phtml), PLACE (available on the worldwide web at dna.affr.go.jp/PLACE) and PLANTCARE (available on the worldwide web at bioinformatics.psb.ugent.be/webtools/plantcare/html/).

Figure 4:
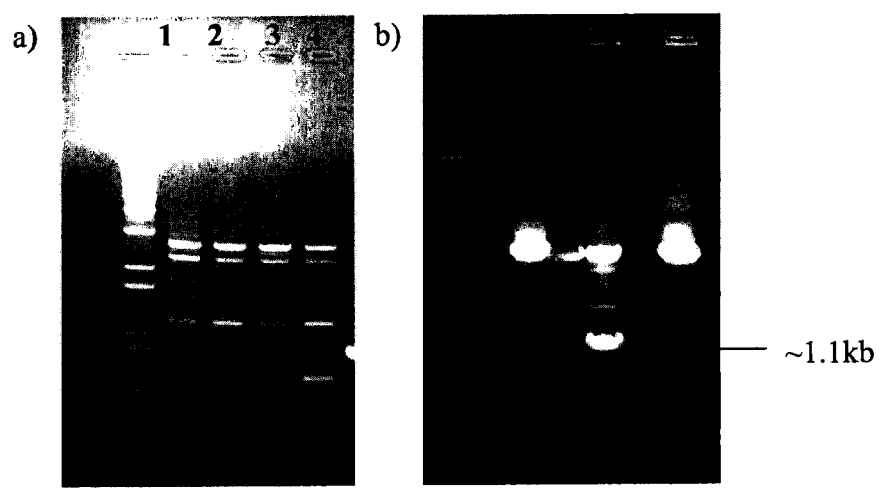
FIG. 4 is a photographic representation of the amplification of UEP1 promoter by genome walking, a) Primary PCR reaction; b) Secondary PCR. Arrow indicates the expected size.

Genome walking was carried out in order to amplify the promoter region of the UEP1 gene. About a 1.1 kb PCR product containing the promoter including a part of coding region of the UEP1 gene was successfully obtained (FIG. 4). The purified PCR product was ligated into PCRII-topo vector (TOPO TA Cloning Kit, Invitrogen Life Technologies) for further manipulation. The recombinant plasmid was designated as pGWUEP1. According to DNA sequences analysis, (NCBI, Softberry, PlantCare, PLACE databases and VNTI software) pGWUEP1 clone was confirmed to encode genomic DNA sequences of UEP1 with size of about 1031 bp. This fragment consist a part of coding and promoter regions of UEP1 gene. The size of coding region is about 203 bp. Detailed analysis showed that a total of 828 residues starting from its translational start sites were identified as part of the uep1 promoter including its 5' untranslated region. The putative location of transcription start site (TSS) was determined using Softberry database. Location of the putative transcription start site was predicted to start at nucleotide Adenine (A) which 100 nucleotides upstream from translational initiation site of the gene. A potential TATA box sequence was identified at −30 upstream of transcription start site. It was also indicated that computational analysis was used to identify features in gene architecture that contributed toward determining the expression level of the UEP1 gene. Results showed that this gene contains a consensus sequence of a ribosomal protein gene including putative UAS and T-rich elements. It also contains other cis-acting elements that associate to light responsive elements, hormone responsive elements (ERE, ABA and MYB) and tissue specific elements. This finding clearly indicates that the UEP1 promoter is controlled by synergism of multiple cis-acting regulatory elements to confer constitutive expression in plant growth and development. The genomic sequences of UEP1 are showed in FIG. 5 and SEQ ID NO 1.

Example 3

Evaluation of Promoter Activity

Construction of the Transformation Vector

Promoter activity can be determined through transient expression studies using a reporter gene such as GUS. The promoter region was cloned into pBI221 plasmid, behind the GUS reporter gene and it replaced the cauliflower mosaic virus (CaMV)35S promoter. Plasmid pBI221 and the CaMV35S promoter fragment (in pCRII-TOPO vector) were digested with Sph1 and Xba1. Digestions were carried out in 100 µl reaction mixtures containing 20 µl DNA, 1× buffer and 5 µl (10 units) restriction enzymes. The digestion mixtures were incubated at 37° C. for overnight. The mixtures were analyzed by gel agarose electrophoresis and the fragment which was obtained was purified using QIAquick Gel Extraction kit (QIAGEN®). The ligation reaction was carried out in mixtures containing of 1 µl of purified pBI221 vector plasmid, 1×T4 ligation buffer, 2 µl T4 ligase and 5 µl purified DNA insert. Sterile water was added to a final volume of 20 µl and the mixture was incubated at 16° C. overnight. The mixture was cloned into One Shot® Chemically Competent *E. coli* cells following the manufacturer's protocol and screening for clones containing recombinant plasmid was carried out by restriction analysis to determine fragment insertion.

Preparation of Target Material for Transformation

Oil palm tissues such as embryogenic calli, embryoid, young leaflet from mature palm (YLMP), green leaves, stem and mesocarp 9 WAA were cultured on solidified agar containing Murashige and Skoog (MS) medium. The agar was macro and micronutrient supplemented with 1 mg/L napthalene acetic acid (NAA) and 30 g/L sucrose. The medium was adjusted to pH 5.7 with NaOH and autoclaved at 121° C. for 15 minutes. Additionally, mesocarps were sterilized in 20% Clorox for 20 min, followed by rinsing three times with sterile distilled water before being cultured. All explants except for embryoids were cut into 5 mm×5 mm disks before being placed into MS medium. All tissues were incubated in the dark at 28° C., 24 hr before bombardment with plasmid DNA.

Bombardment of Oil Palm Tissues

Particle bombardment of plasmid DNA was employed using the BioRad Biolistic PDS-1000/He Particle Delivery System (Bio-Rad, Hercules, Calif. USA). 20 µg DNA, 100 µl 2.5M CaCl2, and 40 µl 0.1M Spermidine were added to each aliquot of 100 µL gold particles. The components were mixed by continuous vortexing which was continued for 3 minutes and followed by centrifugation at 10,000 rpm for 10 seconds. The supernatant was removed and the particles were washed twice with 500 µl v/v 100% ethanol, followed by mixing, and centrifugation at 10,000 rpm for 60 seconds. Finally, the DNA coated gold particles were resuspended in 120 µl absolute ethanol. For each bombardment, 6 µl of DNA coated gold particles were dispensed onto the centre of a macrocarrier and dried under sterile conditions. The target tissues were placed in the centre of an agar containing Petri dish. Transformation was carried out by using a bombardment pressure of 1100 psi; a macrocarrier to stopping screen distance of 6 mm; a target plate distance of 6 cm and a chamber vacuum at 26 inch Hg (Parveez, 1998, supra). The bombarded tissues were incubated in the dark at 28° C., for 48 hours before GUS histochemical analysis.

GUS Histochemical Assay

The GUS assay buffer (0.1M NaPO4 buffer pH7.0, 0.5 mM K-Ferricyanide, 0.5 mM K-Ferrocyanide, 0.01M EDTA, 1 mg/ml X-gluc (5-Bromo-4-Chloro-3-Indolyl-β-D-glucuronide), 1 µl/ml Triton-X and 20% v/v methanol)) (Klein et al, *Nature*. 327:70-73, 1988) was filter sterilized and stored at −20° C. in the dark. Two days after bombardment, the tissues were stained overnight (20 hr) at 37° C. with GUS buffer. For green tissues, post-incubation treatment was performed by soaking the tissue in fresh 70% ethanol 5 times and subsequently incubated at 37° C. until the plant tissues were light green or clear. The chlorophyll was extracted into the ethanol making it easier to see the blue staining of the plant tissue. Blue spots were scored optically using a Nikon UFX-DX system.

Figure 6A:
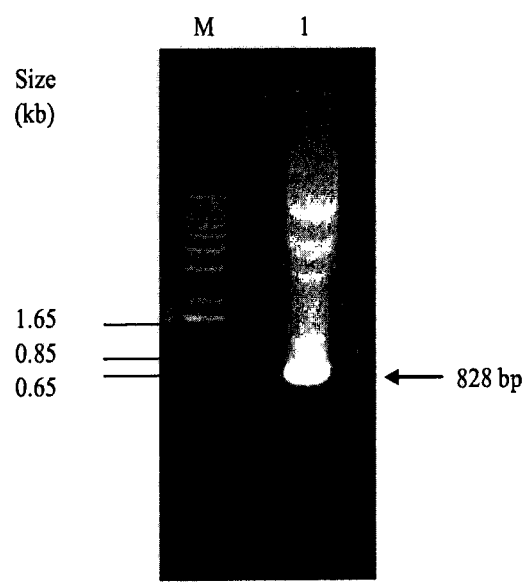
FIG. 6A is amplification of UEP1 promoter region from pGWUEP1 plasmid. The coding region was not included in the amplified fragment. Lane M: 1 Kb Plus DNA Ladder, lane 1: PCR product of the expected promoter region. Arrow indicates the 828 bp fragment.
Figure 6B:
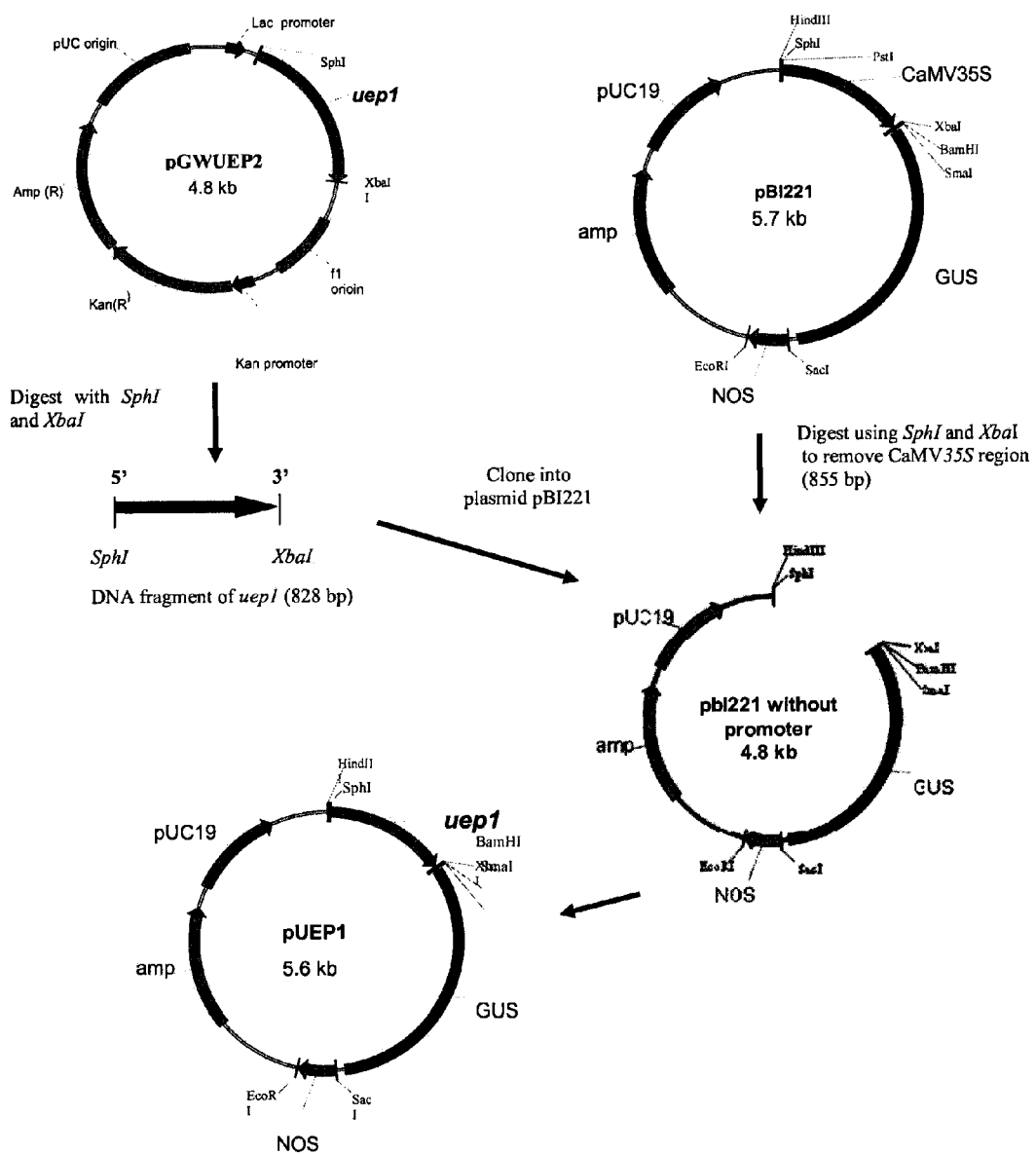
FIG. 6B is a diagrammatical representation of the construction of pUEP1. The pGWUEP1 was digested with Sph1 and Xba1 and UEP1 promoter was cloned into pBI221 by removing the CaMV35S to generate pUEP1. The arrow indicates the orientation of each DNA fragments assembled.

Functional analysis of the promoter was performed through construction of a transformation vector containing gusA as a reporter gene and a nos terminator under the control of the UEP1 promoter. In promoter analysis, the coding region, starting from translation start site should be removed from the fragment. Removing of translation start site is important to avoid undesired translation initiation from the uep1 gene and to ensure the expression of reporter genes occur from its own translational start codon. Promoter and its 5' untranslated region were amplified from plasmid pGWUEP1 (FIG. 6A). The amplification was also used as means to introduce Sph1 site flanking the 5' end and Xba1 site flanking the 3' end. The purified PCR products were then ligated into PCRII-topo vector (TOPO TA Cloning Kit, Invitrogen Life Technologies) to form pGWUEP2 plasmid DNA. In this study, UEP1 promoter was cloned into pBI221 transformation vector (Clontech, USA) by replaced the CaMV35S promoter to form a new transformation vector designated as pUEP1. The construction of pUEP1 was carried out using plasmid DNA pGWUEP2 as illustrated in FIG. 6B. A transient expression study by a histochemical GUS assay was performed to evaluate the activity of the promoter. The pUEP1 vector that carries the UEP1 promoter was bombarded into oil palm tissues including embryogenic calli, embryoid, young leaflet from mature palm (YLMP), green leaf, stem tissues (shoot tip), mesocarp and immature embryo. Plasmid pAHC25 and the original pBI221 which are strong monocot and dicot promoters respectively were included as controls when compared with the pUEP1 promoter. The result indicated that UEP1 functions as constitutive promoter in oil palm plants (*Elaeis*), due to its ability to express GUS in all the tissue that was tested (FIG. 7). Interestingly, this promoter could also be used in dicots system as it capable of driving the expression of GUS in tobacco.

It was demonstrated that UEP1 has high activity but the strength of this promoter was slightly lower than the controls. In order to enhance the promoter effectiveness, the promoter was modified by addition of intron region and ubiquitin monomer behind the GUS reporter gene. This strategy was found to successfully increase the strength of other constitutive promoters in monocotyledonous plants. The endogenous UEP1 promoter can be used as a crucial biotechnology tool for producing ubiquitous expression of transgenes in transgenic oil palm plants (*Elaeis* sp.).

Those skilled in the art will appreciate that the present inventions and disclosures described herein are susceptible to variations and modifications other than those specifically described. It is also to be understood that the present inventions and disclosures include all such variations and modifications. The present inventions and disclosures also include all of the steps, features, compositions and compounds referred to or indicated in this specification, individually or collectively, and any and all combinations of any two or more of said steps or features.

Hood et al., *J. Bacterol.* 168:1291-1301, 1986
Horn et al, *Plant Cell Rep.* 7: 469-472, 1988
Horsch et al, *Science* 27: 1229-1231, 1985
Ikuta et al, *Biotech* 8:241, 1990
Ishida et al, *Nature Biotechnol.* 14: 745-750, 1996

TABLE 2

Comparison of promoter strength on transient gusA gene expression and GUS activity in oil palm tissues two days after bombardment

| Promoter/ Construct | Mean (Standard Error) of GUS foci | | | | | | | |
|---|---|---|---|---|---|---|---|---|
| | YMLP | EC | EM | GL | ST | MS | IE | TB |
| Ubi1/ pAHC25 | 9166.6 ± 119.2 | 121.67 ± 17.68 | 568.8 ± 129.5 | 25.2 ± 6.72 | 62.0 ± 27.7 | 6.7 ± 2.0 | 170 ± 0.0 | 15 ± 11.0 |
| CaMV35S/ pBI221 | 3504.2 ± 133.3 | 100.33 ± 52.1 | 314.0 ± 56.5 | 7.6 ± 2.6 | 85.7 ± 3.23.3 | 2.8 ± 0.6 | — | 33 ± 9.71 |
| uep1/pUEP1 | 1812.0 ± 75.7 | 42.25 ± 5.82 | 237.8 ± 61.95 | 9.6 ± 2.7 | 37.0 ± 11.2 | 2.3 ± 0.5 | 93 ± 14.0 | 12.5 ± 2.5 |

YMLP—Young leaflet from mature palm
EC—Embryogenic calli
EM—Embryoid
GL—Green leaf
ST—Shoot tip (meristematic tissues)
MS—Mesocarp
IE—Immature embryo
TB—Tobacco

BIBLIOGRAPHY

Altchul et al, *Nucleic Acids Res.* 25:3389-3402, 1997
Arencibia et al, *Plant Cell Rep.* 14: 305-309, 1995
Barcelo et al, *The Plant Journal* 5: 583-592, 1994
Barker et al, *Plant Mol. Biol.* 2:141-146, 1983
Bechtold et al, *C. it Acad. Sci. Paris.* 316: 1194-1199, 1993
Bevan et al, *Nature* 304: 184-187, 1983
Bower and Birch, *The Plant Journal* 2: 409-416, 1992
Bytebier et al, *Proc. Natl. Acad. Sci. USA* 84, 5345-5349, 1987
Casas et al, *Plant Breed. Rev.* 13: 235-264, 1995
Castillo et al, *Bio/Technology* 12:1366-1371, 1993
Chee et al, In Gelvin and Schilperoot (eds.) *Plant Molecular Biology Manual.* Boston: Kluwer Academic Pub, pp. C3: 1-28, 1991
Chowdhury et al, *Plant Cell Rep.,* 16: 277-281, 1997
Christensen and Quail, *Plant Mol Biol* 12:619-632, 1989
Christiensen, and Quail, *Transgenic Research* 5:213-218, 1996
Christou et al, *Bio/Technol.* 9: 957-962, 1991
Christou, *The Plant J.* 2:275-281, 1992
D'Halluin et al, *The Plant Cell* 4: 1495-1505, 1992
Datta et al, Peterhans, *Bio/Technol.* 8: 736-740, 1990
DeBlock et al, *EMBO J.* 6: 2513-2518, 1987
DeCleene, and Deley, *Bot. Rev.* 42:389-466, 1976
Dellaporta et al, *In: Chromosome Structure and Function* pp 263-282, 1988
Doyle, & Doyle, *Phytochemical Bulletin* 19: 11-15, 1987
Eeuwens, *Physiol. Plant.* 36: 23-28, 1976
Ellis, *Vegetables and Vegetable Prod.* 16: 117-160, 1993
Feinberg, and Vogelstein, *Analytical Biochem.* 137: 266-267, 1984
Fraley et al, *Proc. Natl. Acad. Sci. USA* 80: 4803-4807, 1983
Frame et al, *The Plant Journal* 6: 941-948, 1994
Fromm et al, *Bio/Technol.* 8: 833-838, 1990
Garfinkel et al, *Cell* 27:141-153, 1983
Greve, *J. Mol. Appl. Genet.* 1:499-511, 1983
Guo et al, *Physiol. Plant.* 93: 19-24, 1995
Hinchee et al, *Bio/Technol* 6: 915-922, 1988
Hoekema et al, *Nature.* 303: 179-180, 1983
Jaime et al, *Theor. Appl. Genet.* 89:525-533, 1994
Jaime et al, *Euphytica:* 85:35-44, 1995
Janssen and Gardner, *Plant Mal. Biol.* 14: 61-72, 1989
Jefferson, *Plant Mol. Biol. Rep.* 5: 387-405, 1987
Kaepler et al, *Plant Cell Rep.* 9: 415-418, 1990
Katz et. al, *J. Gen. Microbiol.* 129:2703, 1983
Klein et al, *Nature.* 327:70-73, 1988
Klein et al, *Proc. Natl. Acad. Sci. USA.* 85: 8502-8505, 1988
Klein et al, *Nature.* 327: 70-73, 1987
Kloti et al, *Plant Cell Rep.* 12: 671-675, 1993
Konez and Schell, *Mol. Gen. Genet.* 204: 383-396, 1986
Kuehnle, and Sugii, *Plant Cell Rep.* 11: 484-488, 1992
Last et al, *Theor Appl Genet.* 81:581-588, 1991
Laursen et al, *Plant Mol. Biol.* 24: 51-61, 1994
Lazo et al, *Biotechnology* 9: 963-967, 1991
Lorz et al, *Mol. Gen. Genet.* 199: 178-182, 1985
Lowe et al, *Bio/Technol.* 13: 677-682, 1995
May et al, *Bio/Technol.* 13: 486-492, 1995
McElroy et al, *Plant Cell.* 2:163-171, 1990
Meijer et al, *Plant Mol. Biol.* 16:807-820, 1991
Meinkoth and Wahl, *Anal. Biochem,* Vol. 38:267-284, 1984
Mindrinos et al, *Cell* 78:1089, 1994
Moore et al, *J. Mol. Biol.* 272:336-347, 1997
Mullis et al, *Methods Enzymol.* Vol. 55:335-350, 1987
Murashige, and Skoog, *Physiol. Plant.* 15:473-97, 1962
Murray et al, *Nucleic Acids Res.* 17:477-498, 1989
Myers and Miller, *CABIOS* 4:11-17, 1988
Needleman and Wunsch, *J. Mol. Biol.* 48:443-453, 1970
Niedz et al, *Plant Cell Reports* 14:403, 1995
Ow et al, *Science* 234:856, 1986
Paranjothy et al, In International Palm Oil Development Conference held in Kuala Lumpur, 5-9 Sep. 1989: Proceeding edited by Sukaimi, Zakaria, Paranjothy, Darus, Rajanaidu, Cheah, Wahid and Henson. Bangi, *Palm Oil Research Institute of Malaysia,* pp. 109-121, 1989
Parveez, PhD. Thesis. Universiti Putra Malaysia, 1998
Paszkowski et al, *EMBO J.* 3:2717-2722, 1984
Pearson and Lipman, *Proc. Natl. Acad. Sci.* 85:2444-2448, 1988
Pearson et al, *Meth. Mol. Biol.* 24:307-331, 1994
Potenza et al, *In Vitro Cell. Dev. Biol. Plant* 40:1-22, 2004

Potrykus, *Bio/Technol.* 8: 535-542, 1990
Potrykus et al, *Mol. Gen. Genet.* 199: 183-188, 1985
Prasher et al, *Biochem. Biophys. Res. Comm.* 126:1259, 1985
Rajanaidu, and Jalani. In Proceedings of 1995 PORIM National Oil Palm Conference.—Technologies in Plantation, The Way Forward. 11-12 Julai 1995. Kuala Lumpur: *Palm Oil Research Institute of Malaysia*, pp. 1-29, 1995
Rashid et al, *Plant Cell Rep.* 15: 727-730, 1996
Ravigadevi et al, In Advances in Oil Palm Research, (eds). Yusof, Jalani, and Chan. *Malaysia Palm Oil Board.* 1:284-331, 2000
Rhodes et al, *Science.* 240: 204-207, 1988
Riggs et al, *Proc. Natl. Acad. Sci. USA* 83:5602-5606, 1986
Riggs et al, *Nucleic Acids Res.* 75 (19):8115, 1987
Ritala et al, *Plant Mol. Biol.* 24: 317-325, 1994
Salomon et al, *EMBO J.* 3:141-146, 1984
Sambrook et al, Molecular Cloning: A Laboratory Manual (2d ed., Cold Spring Harbor Laboratory Press, Cold Spring Harbor, N.Y.), 1989
Sambrook et al, *Molecular cloning: A laboratory manual.* 2nd Ed. Cold Spring Harbor Laboratory Press. USA, 1989
Schnorf et al, *Transgenic Research* 1: 23-30, 1991
Schubert et al, *J. Bacteriol.* 170:5837-5847, 1988
Shaw et al, *Science* 233:478-481, 1986
Shimamoto et al, *Nature.* 338: 274-276, 1989
Smith et al, *Adv. Appl. Math.* 2:482, 1981
Southern, *J. Mol. Biol.* 98: 503-517, 1975
Stalker et al, *Science* 242:419-423, 1988
Stemmer, *Nature* 370:389-391, 1994
Stemmer, *Proc. Natl. Acad. Sci. USA* 91: 10747-10751, 1994
Sutcliffe, *Proc. Natl. Acad. Sci. USA* 75:3737, 1978
Tarmizi et al, Establishment of oil palm suspension cultures from calli derived from various sources. *Proc.* 11th *National Biotechnology Seminar,* 22-24 Nov. 1999, Melaka Malaysia, pp. 381-382, 1999
Thillet et al, *J. Biol. Chem.* 263:12500, 1988
Tijssen, *Laboratory Techniques in Biochemistry and Molecular Biology-Hybridization with Nucleic Acid Probes*, Part II Chapter 2 (Elsevier, New York), 1993
Tomes et al, *In Plant Cell, Tissue, and Organ Culture: Fundamental Methods*, ed. Gamborg and Phillips (Springer-Verlag, Berlin), 1995
Topfer et al, *The Plant Cell* 1: 133-139, 1989
Van Damme et al, *Plant Mol. Biol.* 24:825, 1994
Vancanneyt et al., *Mol Gen Genet,* 220, 245-250, 1990
Vasil et al, *Bio/Technol.* 10: 667-674, 1992
Waldron et al, *Plant Mol. Biol.* 5:103-108, 1985
Walker and Gaastra, eds. Techniques in Molecular Biology (MacMillan Publishing Company, New York), 1983
Wang et al, *Bio/Technol.* 10: 691-696, 1992
Weber et al, *Physiol. Plant.* 79: 190-193, 1990
Weber et al, *Eur. J. Cell. Biol.* 49: 73-79, 1989
Weissbach and Weissbach, In: Methods for Plant Molecular Biology, (Eds.), Academic Press, Inc., San Diego, Calif., 1988
Xiao et al, *Molecular Breeding,* 15:221-231, 2005
Xiayi et al, *Transgenic Research* 5: 219-221, 1996
Xu, and Li, *Plant Cell Rep.* 13:237-242, 1994
Zambryski et al, *EMBO J.* 2: 2143-2150, 1983
Zeng and Yang, *Plant. Mol. Biol. Rep.* 20:417a-417e, 2002
Zhang et al, *Proc. Natl. Acad. Sci. USA* 94:4504-4509, 1997
Zhijian et al, *Plant Science* 708:219-227, 1995
Zukowsky et al, *Proc. Natl. Acad. Sci. USA* 80:1101, 1983

The invention claimed is:

1. A DNA construct comprising a nucleic acid molecule operably linked to a heterologous nucleotide sequence of interest; wherein the nucleic acid molecule comprises the nucleotide sequence set forth in SEQ ID NO:2 or the full-length complement thereof.

2. A plant cell having stably incorporated into its genome the DNA construct of claim 1.

3. The plant cell of claim 2, wherein said plant cell is from a monocot.

4. The plant cell of claim 3, wherein said monocot is a species of *Elaeis*.

5. The plant cell of claim 2, wherein said plant cell is from a dicot.

6. A plant having stably incorporated into its genome the DNA construct of claim 1.

7. The plant of claim 6, wherein said plant is a monocot.

8. The plant of claim 7, wherein said monocot is a species of *Elaeis*.

9. The plant of claim 6, wherein said plant is a dicot.

10. A genetically modified seed of the plant of claim 6, wherein the seed comprises the DNA construct.

11. The plant of claim 6, wherein the heterologous nucleotide sequence of interest encodes a gene product or a double-stranded RNA that confers resistance to a herbicide, resistance to a pest, or resistance to disease, or confers a modification to the levels or composition of lipid and non-lipid components of palm oil.

12. A method for expressing a nucleotide sequence in a plant, said method comprising introducing into a plant a nucleic acid molecule operably linked to a heterologous nucleotide sequence of interest, wherein said nucleic acid molecule comprises the nucleotide sequence set forth in SEQ ID NO:2.

13. The method of claim 12, wherein said plant is a monocot.

14. The plant cell of claim 12, wherein said plant is a dicot.

15. The method of claim 12, wherein the heterologous nucleotide sequence encodes a gene product or a double-stranded RNA that confers resistance to a herbicide, resistance to a pest, or resistance to disease, or confers a modification to the levels or composition of lipid and non-lipid components of palm oil.

16. A method for expressing a nucleotide sequence in a plant cell, said method comprising introducing into a plant cell a DNA construct comprising a nucleic acid molecule operably linked to a heterologous nucleotide sequence of interest, wherein said nucleic acid molecule comprises the nucleotide sequence set forth in SEQ ID NO:2.

17. The method of claim 16, wherein said plant cell is from a monocot.

18. The method of claim 17, wherein said monocot is a species of *Elaeis*.

19. The plant cell of claim 16, wherein said plant cell is from a dicot.

20. The method of claim 16, wherein the heterologous nucleotide sequence encodes a gene product or a double-stranded RNA that confers resistance to a herbicide, resistance to a pest, or resistance to disease, or confers a modification to the levels or compositions of lipid and non-lipid components of palm oil.

21. The method of claim 16, wherein expression of said heterologous nucleotide sequence alters the phenotype of said plant cell.

22. The method of claim 21, wherein the plant cell is from a monocot.

23. The method of claim 22 wherein the monocot is *Elaeis*.

24. The method of claim 21, wherein said plant cell is from a dicot.

* * * * *